(12) United States Patent
Tegg et al.

(10) Patent No.: US 12,048,478 B2
(45) Date of Patent: Jul. 30, 2024

(54) ONE FIBER FORCE AND SHAPE SENSING

(71) Applicant: St. Jude Medical International Holding S.à r.l., Luxembourg (LU)

(72) Inventors: Troy T. Tegg, Elk River, MN (US); Jacob J. Daly, Blaine, MN (US)

(73) Assignee: St. Jude Medical International Holding S.à.r.l., Luxembourg (LU)

( * ) Notice: Subject to any disclaimer, the term of this patent is extended or adjusted under 35 U.S.C. 154(b) by 685 days.

(21) Appl. No.: 16/435,210

(22) Filed: Jun. 7, 2019

(65) Prior Publication Data
US 2019/0374282 A1 Dec. 12, 2019

Related U.S. Application Data

(60) Provisional application No. 62/719,811, filed on Aug. 20, 2018, provisional application No. 62/682,517, filed on Jun. 8, 2018.

(51) Int. Cl.
| | |
|---|---|
| *A61B 18/14* | (2006.01) |
| *A61B 18/00* | (2006.01) |
| *A61B 34/20* | (2016.01) |
| *A61B 34/30* | (2016.01) |
| *A61B 90/00* | (2016.01) |

(52) U.S. Cl.
CPC .......... *A61B 18/1492* (2013.01); *A61B 34/20* (2016.02); *A61B 34/30* (2016.02); *A61B 90/06* (2016.02); *A61B 2018/00577* (2013.01); *A61B 2034/2061* (2016.02); *A61B 2090/065* (2016.02); *A61B 2562/0266* (2013.01)

(58) Field of Classification Search
CPC ...... A61B 18/1492; A61B 2018/00577; A61B 2034/2061; A61B 2090/065; A61B 34/20; A61B 34/30; A61B 90/06; A61B 2562/0266

See application file for complete search history.

(56) References Cited

U.S. PATENT DOCUMENTS

| | | | |
|---|---|---|---|
| 5,152,748 A * | 10/1992 | Chastagner | A61B 10/06 604/95.05 |
| 8,182,433 B2 | 5/2012 | Leo et al. | |
| 8,622,935 B1 | 1/2014 | Leo | |
| 8,649,847 B1 * | 2/2014 | Park | A61M 25/0105 604/95.05 |

(Continued)

FOREIGN PATENT DOCUMENTS

| | | |
|---|---|---|
| WO | 2010011820 A2 | 1/2010 |
| WO | 2017/118949 A1 | 7/2017 |

*Primary Examiner* — Joseph A Stoklosa
*Assistant Examiner* — Annie L Shoulders
(74) *Attorney, Agent, or Firm* — Armstrong Teasdale LLP

(57) ABSTRACT

A medical device, system, and method having a flexible shaft and a multi-core fiber within the flexible shaft. The multi-core fiber includes a plurality of optical cores dedicated for shape sensing sensors, and a plurality of optical cores dedicated for force sensing sensors. A tip assembly can comprise a tip electrode and a coupler comprising at least one fiber support tube center. A distal portion of the coupler can be coupled to a proximal portion of the tip electrode. The tip assembly can further comprise a multi-core fiber comprising a plurality of cores and a fiber support tube. A proximal portion of the fiber support tube can be coupled to the at least one fiber support tube center.

20 Claims, 18 Drawing Sheets

(56) References Cited

U.S. PATENT DOCUMENTS

| | | |
|---|---|---|
| 2004/0181138 A1 | 9/2004 | Hindricks et al. |
| 2007/0151391 A1 | 7/2007 | Larkin et al. |
| 2008/0071267 A1 | 3/2008 | Wang et al. |
| 2009/0177095 A1* | 7/2009 | Aeby ............ A61B 17/320758 600/478 |
| 2010/0041986 A1* | 2/2010 | Nguyen ............... A61B 5/6852 600/427 |
| 2010/0249601 A1* | 9/2010 | Courtney ............ A61B 5/6852 600/463 |
| 2014/0081264 A1 | 3/2014 | Fandrey et al. |
| 2014/0276759 A1* | 9/2014 | Kim ................... A61B 18/1492 606/33 |
| 2017/0209209 A1* | 7/2017 | Govari .............. A61B 18/1206 |
| 2018/0338859 A1* | 11/2018 | Mirsepassi .............. A61B 1/07 |
| 2018/0338860 A1* | 11/2018 | Farley .................. A61F 9/0017 |
| 2019/0021756 A1* | 1/2019 | Boudreaux ...... A61B 17/00234 |
| 2020/0238051 A1* | 7/2020 | Hwang ................ A61B 5/0084 |

* cited by examiner

ONE FIBER FORCE AND SHAPE SENSING

CROSS-REFERENCE TO RELATED APPLICATIONS

This application claims the benefit of U.S. provisional application No. 62/682,517, filed 8 Jun. 2018, and U.S. provisional application No. 62/719,811, filed 20 Aug. 2018, both of which are hereby incorporated by reference as though fully set forth herein.

BACKGROUND a. Field

This disclosure relates to medical devices, and particularly to interventional and/or surgical catheters and other elongate medical devices capable of being visualized within a body as well as providing responsive feedback concerning tissue contact with a distal portion of the medical device.

b. Background

Within a cardiac cycle, the human heart experiences electrical impulses traversing from the sinus node to the ventricles. Cardiac contraction is driven by a cycle of polarization and depolarization as electrical currents spread across the heart. In healthy hearts, the heart will experience an orderly progression of depolarization waves called sinus rhythm. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to diagnose and correct conditions such as atrial arrhythmia, including for example, ectopic atrial tachycardia, atrial fibrillation, and atrial flutter. Typically, in atrial fibrillation therapies, a catheter is manipulated through a patient's vasculature to the patient's heart carrying one or more electrodes which may be used for mapping, ablation, diagnosis, or other treatment. Where an ablation therapy is desired to alleviate symptoms of atrial fibrillation, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio-frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess force between the ablation catheter tip and the targeted myocardial tissue may result in excessive ablation which may permanently damage the cardiac muscle and/or surrounding nerves. When contact force between the ablation catheter tip and the targeted myocardial tissue is below a target force, the efficacy of the ablation therapy may be reduced, or entirely negated.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact force between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation and determine the efficacy of a treatment. Similarly, ablation controller circuitry has improved the consistency of individual ablation therapies. There are devices that attempt to measure the force exerted between myocardial tissue and the ablation catheter tip. Existing designs utilize ablation catheter tips with deformable bodies which deform in response to a force being exerted on the ablation catheter tip. Sensors (e.g., magnetic, optical, etc.) are used to approximate the deformation of the deformable body and to output a signal to controller circuitry that associates the deformation with a force exerted by the ablation catheter tip. However, existing deformable body designs suffer from both complexity and cost, primarily related to acquisition and delivery of the measurement signal to the proximal end of the catheter.

The foregoing discussion is intended only to illustrate the present field and should not be taken as a disavowal of claim scope.

BRIEF SUMMARY

The present disclosure relates to medical devices, and particularly to interventional and/or surgical catheters and other elongate medical devices capable of being visualized within a body as well as providing responsive feedback concerning tissue contact with a distal portion of the medical device.

In one embodiment, a tip assembly can comprise a tip electrode and a coupler comprising at least one fiber support tube center. A distal portion of the coupler can be coupled to a proximal portion of the tip electrode. The tip assembly can further comprise a multi-core fiber comprising a plurality of cores and a fiber support tube. A proximal portion of the fiber support tube can be coupled to the at least one fiber support tube center.

In another embodiment, a tip assembly can comprise a multi-core fiber comprising a plurality of cores and a fiber support tube, a coupler comprising a first fiber support tube center, and a flex tip comprising a second fiber support tube center. The flex tip can be coupled to a distal portion of the coupler and the fiber support tube can be coupled to the first fiber support tube center and the second fiber support tube center.

In yet another embodiment, a tip assembly can comprise a multi-core fiber comprising a plurality of cores and a fiber support tube, a coupler comprising a first fiber support tube center, a fluid cap comprising a central channel and at least one electrical channel, wherein the fluid cap is coupled to a proximal end of the coupler, an irrigation lumen coupled to the fluid cap, and a tip electrode coupled to a distal portion of the coupler. The multi-core fiber can be disposed within an interior portion of the irrigation lumen, the first fiber support tube and the second fiber support tube can be disposed within an interior portion of the tip assembly, and the fiber support tube can be coupled to the first fiber support tube center and the second fiber support tube center.

The foregoing and other aspects, features, details, utilities, and advantages of the present disclosure will be apparent from reading the following description and claims, and from reviewing the accompanying drawings.

DETAILED DESCRIPTION

In the following description, reference is made to the accompanying drawings that depict representative examples. It is to be understood that other embodiments and implementations may be utilized, as structural and/or operational changes may be made without departing from the scope of the disclosure. Like reference numbers are used throughout the disclosure where appropriate.

The disclosure is generally directed to medical devices. Devices and techniques are disclosed relating to interventional and/or surgical catheters, introducers, and other elongate medical devices capable of being visualized within a body, as well as being capable of providing responsive feedback concerning tissue contact with a distal portion of the medical device.

In one embodiment, a catheter or other elongate medical device is equipped with distal force sensing capabilities and elongate body shape sensing capabilities. In one embodiment, the distal force sensing and elongate body shape sensing capabilities are implemented with optical sensing technology. Such optical sensing technologies may involve different optical sensing technologies, such as, for example, fiber Bragg grating (FBG) shape sensing and optical interferometer distal force sensing. However, embodiments described herein using optical conduits (e.g., optical fibers, fiber cores, etc.) may utilize any optical technologies that transmit light via such optical conduits for use in the force and shape sensing mechanisms, whether the implemented force and shape sensing technologies are the same or dissimilar.

Representative embodiments described herein also involve implementing a multi-core fiber(s) to provide the optical conduits through some or all of the catheter or other elongate body.

Figure 1:
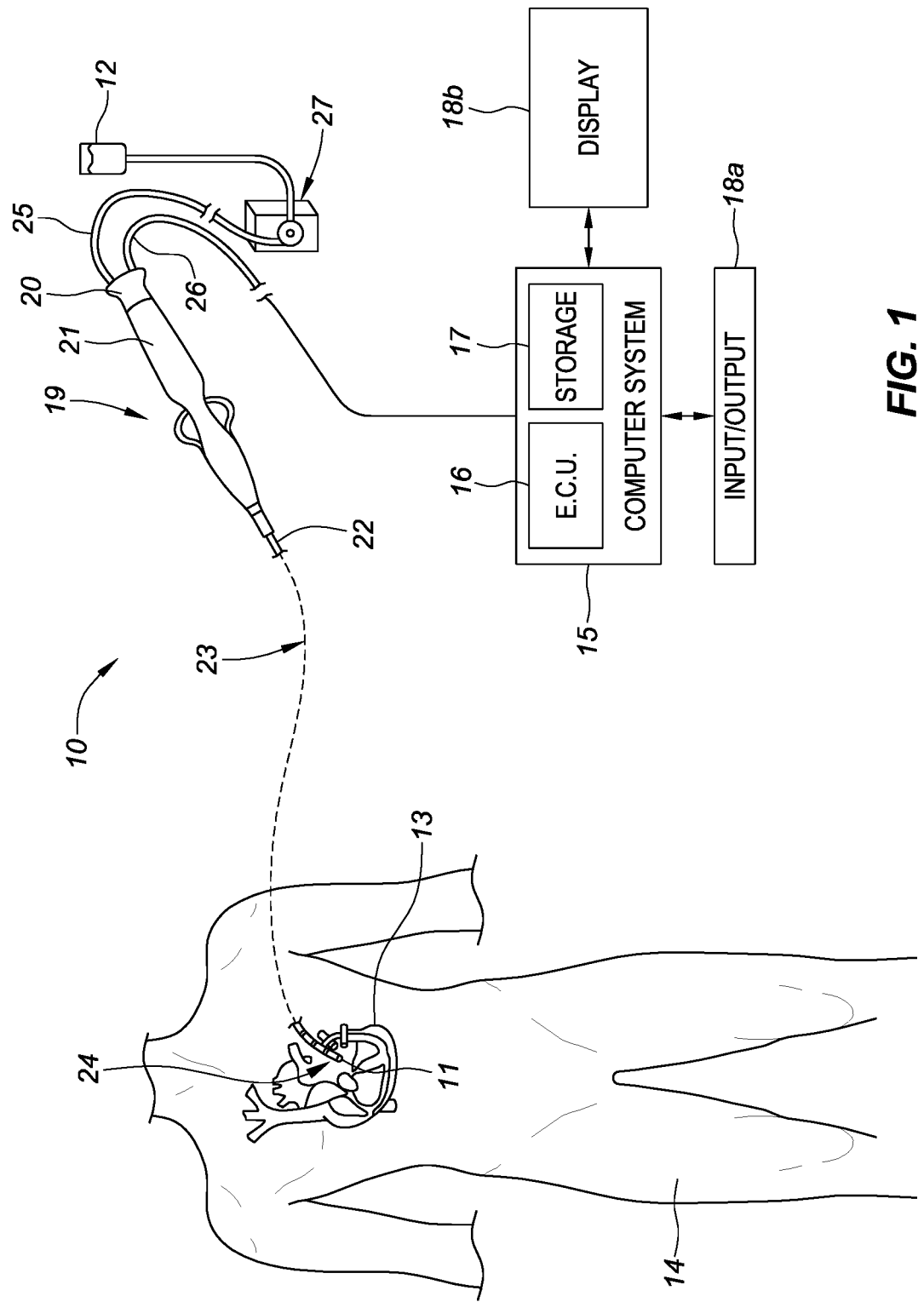
FIG. 1 is a diagrammatic view of a system that can be used to perform an interventional medical procedure.

FIG. 1 illustrates a representative system 10 that may be used in an interventional medical procedure on a body 14. While the description herein may be described in terms of a particular representative medical procedure and/or body 14 organ(s), it should be recognized that the principals described herein are equally applicable to other procedures and body organs. For example, while portions of the description may be described in terms of cardiac procedures and/or in terms of endocardial procedures involving the human heart, the principals described herein are equally applicable to other interventional procedures, such as epicardial procedures, renal denervation or other procedures involving the kidneys, vascular procedures, and the like.

Referring to FIG. 1, the system 10 includes a medical device, such as a catheter 19, introducer, or other interventional or surgical device where at least a portion of the device is placed within the body 14. The representative catheter 19 includes a catheter electrode assembly 11 shown within the cardiac space within the body 14, where the electrode assembly 11 is included as part of the catheter 19 or other medical device and may be used, for example, for diagnosis, visualization, and/or treatment of tissue 13 (such as cardiac or other tissue) in the body 14. For example, the electrode assembly 11 may be used for ablation therapy of tissue 13 and/or mapping purposes in a patient's body 14.

FIG. 1 further shows various representative sub-systems included in the overall system 10. The system 10 may include a main computing system 15, which may include a processing system, depicted in FIG. 1 as an electronic control unit (E.C.U.) 16 which represents any individual or distributed processing unit. The computing system 15 may also include data storage 17, e.g., memory and/or other storage. The computer system 15 may further include conventional interface components, such as various user input/output mechanisms 18a and a display(s) 18b, among other components. Information obtained and/or provided by the electrode assembly 11 may be processed by the computer system 15, and may provide data to the clinician via the input/output mechanisms 18a and/or the display 18b, or in other ways as described herein or known in the art.

In the illustrative embodiment, the catheter 19 may include one or more cable connectors or other interface 20, a handle 21, an elongate (e.g., tubular) body or shaft 22 having a proximal portion 23 and a distal portion 24. The distal portion 24 does not represent any particular length, but rather distinguishes some usable portion of the shaft 22 within the body 14 from a remainder of the shaft 22 that ultimately couples to the handle 21 or other control mechanism (e.g., robotic controller). The catheter 19 may also include other conventional components not illustrated herein such as a temperature sensor(s), additional electrodes, corresponding conductors or leads, etc. The connector 20 may provide mechanical, fluid, optical and/or electrical connections for cables, such as cables 25, 26. In the case of an irrigated catheter, a cable(s) 25 may extend from a fluid reservoir 12 and fluid pump 27, and the computer system 15. The connector 20 may comprise conventional components known in the art and, as shown in the illustrated embodiment, may be disposed at the proximal end of the catheter 19.

In the case of a manually controlled catheter, a handle 21 provides a portion for a user to grasp or hold the catheter 19, and may further provide a mechanism for steering or guiding the shaft 22 within the patient's body 14. For example, the handle 21 may include a mechanism configured to change the tension on a pull-wire(s) extending through the catheter 19 to the distal portion 24 of the shaft 22, or may include some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the electrode assembly 11 or elsewhere along the shaft 22. For example, if contact to tissue 13 is made by the electrode assembly 11, any one or more of the handle 21, computing system 15, I/O 18a and/or display 18b may include graphical output, light-emitting-diodes or other visual indicators, tone generator, a vibrating mechanical transducer, and/or other indicator(s), the outputs of which could vary in proportion to the signal sensed at the electrode assembly.

The system 10 of FIG. 1 is merely an exemplary system described to provide a representative context in which the principals described herein may be utilized. Catheter-based diagnostic and treatment systems have been widely used for exploration and treatment of various organs or vessels. Such catheters are typically introduced through a vessel leading to the cavity of the organ to be explored or treated, or alternatively may be introduced in other ways such as directly through an incision made in the wall of the organ. This treatment avoids the trauma and extended recuperation times typically associated with open surgical procedures. For purposes of illustration, descriptions below may be described in representative context of a cardiac ablation procedure using an ablation catheter.

In order to provide effective diagnosis or therapy, the areas to be treated may first be mapped. Such mapping may be performed, for example, when it is desired to selectively ablate current pathways within the heart to treat atrial fibrillation or other electrical cardiac conduction issues. Often, the mapping procedure is complicated by difficulties in locating the zone(s) to be treated due to periodic movement of the heart throughout the cardiac cycle. Current systems rely on manual feedback of the catheter and/or impedance measurements to determine when the catheter is properly positioned in the vessel or organ. Better procedure efficacy may be obtained by measuring contact forces with the vessel or organ wall or detecting contact forces applied by the catheter against the organ or vessel wall that may modify the true wall location. For radio frequency (RF) ablation treatment, sustained contact force is beneficial as less contact force may result in poor ablation, and too much force can result in safety issues such as perforating the organ. Thus, it is desirable to provide apparatuses and methods for detecting and monitoring contact forces between a catheter and the wall of the organ or vessel to permit faster and more accurate diagnostic and treatment.

Force sensing technology can be very difficult to build. This difficulty can lead to poor yields in manufacturing. In Fabry-Perot sensors, the low manufacturing yields can be caused by the low cleave angle required to allow for a usable signal strength. The design of the force sensors can also be limited by the axial displacement of the sensor. The amount of axial displacement detected by the system is not only very difficult to work with on the measurements, it can also be very temperature dependent. Further, current force sensor technology can be susceptible to humidity, IE fluid ingress. For example, with Fabry-Perot sensors, fluid ingress can cause microbubbles to form in the fiber gap/at end of the fiber faces.

As described in greater detail below, one such contact force technology involves optical sensors, such as sensors based on fiber Bragg grating. A fiber Bragg grating (FBG) is a desirable sensor for measuring the force for numerous reasons, such as it does not interfere with electronics and is compact in size. The FBG is a type of distributed Bragg reflector constructed in a segment of optical fiber that reflects particular wavelengths of light and transmits all others. This is achieved by creating a periodic variation in the refractive index of the fiber core thorough two light beams interfering. All wavelength lights have weak reflections at refractive index fringes, but only those wavelengths with phase matching condition will reflect back due to resonance effect and all other wavelength will transmit through the fiber.

For a grating with a period of Λ and fiber core effective index $n_{eff}$, the Bragg wavelength $\lambda_B$ is determined by the resonance condition as $$\lambda_B = 2 n_{eff} \Lambda \qquad (1)$$

When a strain is applied to the fiber grating or ambient temperature changes, both the grating period and the fiber effective index will change accordingly, and hence the Bragg wavelength will shift to blue or red wavelength sides. By measuring the shift of the Bragg wavelength, the FBGs can be used for force and temperature sensing. One advantage derives from the absolute nature of the information-encoding in measuring the wavelength shift, which renders the sensor independent from fluctuating light power or connector losses. With an applied strains and the ambient temperature change dT, the shift of the Bragg wavelength is obtained by differential Eq. (1) as $$\frac{d\lambda}{\lambda_B} = (1 - \rho_e)\varepsilon + (\xi + \alpha)dt \qquad (2)$$

where $$\rho_e = -\frac{1}{n_{eff}} \frac{\partial n_{eff}}{\partial \varepsilon}$$

is the photo-elastic constant; $\rho_e = 0.22$ for pure silica glass.

$$\alpha = \frac{1}{\Lambda} \frac{\partial \Lambda}{\partial T} \sim 0.5 \times 10^{-6}$$

is the coefficient of linear expansion, $$\xi = \frac{1}{n_{eff}} \frac{\partial n_{eff}}{\partial T} \sim 7 \times 10^{-6}$$

is the thermo-optic coefficient, and dT is the temperature change. For a grating at 1550 nm wavelength, the wavelength shifts are typically of order $\sim 1^{pm/\mu\epsilon}$ for strain, and $10^{pm/°C.}$ for temperature.

The Yong's modules E is defined as $$E = \frac{\text{stress}}{\text{strain}} = \frac{F/A_0}{\Delta L/L_0} \quad (3)$$

Where, F is the force, $A_0$ is the area of the fiber cross section, $L_0$ is the fiber length and $\Delta L$ is stressed length due to the applied force. The force is thus derived from Eq. (3) as $$F = EA_0\varepsilon \quad (4)$$

where $\varepsilon = \Delta L/L_0$ is the stain. For a single mode fiber with a diameter of 125 um, the Yong's modulus of the glass material is $70 \times 10^9$ N/m², then the force with respect to the fiber strain is obtained as $$F = 859\varepsilon(N) \quad (5)$$

When the ambient temperature remains unchanged dT=0, for a pure glass $\rho_e=0.22$, submit Eq. (5) into Eq. (2), the applied force with respect to the shift of the Bragg wavelength is obtained as $$F \approx 1101 d\lambda/\lambda_B \quad (6)$$

For a resolution of 0.01 nm Bragg wavelength shift in 1550 nm wavelength band, the force resolution is given by Eq. (6) as 0.7 gram.

Submit Eq. (4) into Eq. (2), the shift of Bragg wavelength with respect to the applied force and temperature change is expressed as $$\frac{\Delta\lambda}{\lambda_B} = (1-\rho_e)\frac{F}{EA_0} + (\xi+\alpha)\Delta T \quad (7)$$

Where $\Delta\lambda$ is the shift of Bragg wavelength, $\Delta T$ is the temperature change, F is the applied force, E is the Yong's module, $A_0$ is the area of fiber cross section, $\rho_e$ is the photo-elastic constant, $\alpha$ is the coefficient of linear expansion, $\xi$ is the thermo-optic coefficient.

To sense three-dimensional (3D) vector force and temperature, four independent sensors may be used in one embodiment. Four single FBGs can be used for the sensing, but ample space may be needed to mount the four FBGs. Additionally, all four FBGs may also involve separate calibration due to mechanical assembly, which limits the FBGs for sensing applications, especially in catheter applications as the size of the catheter tip may be only a few millimeters. The present disclosure describes a multi-core fiber comprising multiple core fibers that run the length of the fiber. The multi-core fiber can assist in limiting the cross-sectional space required within a catheter body for a plurality of independent channels as described herein.

In accordance with one embodiment, when an FBG is inscribed on a multi-core fiber (MCFBG), e.g. at least four core fibers, four FBGs on four fiber cores can act as four sensors, but the overall size still corresponds to that of the single mode fiber. There can be no separate calibration issue, as all four FBGs are in the same fiber. If all cores are constructed substantially the same, the temperature change will correspondingly shift all four Bragg wavelengths, while only the force in the fiber axis direction will shift four Bragg wavelengths in the same mount. When force is applied to the MCFBGs with an angle, the fiber will be bent, and thus four FBGs will experience different compression and tension respectively while the Bragg wavelengths will shift to either short or long wavelengths depending on the force amplitude and its direction. In one embodiment, the end surface of MCFBGs is melted or otherwise amalgamated (e.g., into a ball) to minimize the reflection.

In another embodiment, the catheter can comprise a multi-core fiber that has seven cores, the overall diameter of this fiber can be 155 microns or ~0.006" each core is 6 microns. In one embodiment, all seven cores of the fiber can have gratings. In other embodiments, less than seven cores of the fiber can have gratings. Three of the outer cores can be monitored for force sensing and can be spaced at 120° from one another and the other three outer cores can be used for shape sensing. The last core in the center of the fiber can be used as temperature compensation/internal strain monitoring. If force is applied in a lateral direction one of the three cores can be put into a strech strain and two of the three cores can be put into compression strain. Further, if force is applied in an axial direction, all three cores can be placed into compression strain. In another embodiment, six of the outer cores can be monitored for force sensing and can be spaced at 60° from one another. In one embodiment, the center core can be used as temperature compensation/internal strain monitoring while the six outer cores are used for force sensing. In yet another embodiment, six cores can be used for monitoring a force imparted on a distal portion of the mulit-core fiber while all or a subset of the cores can have additional sensors proximal of the force sensing portion for determining or sensing a shape of the multi-core fiber. In this embodiment, a core can be used for both shape sensing and force sensing. Various configurations could be used. In some configurations all of the cores could be used for both shape sensing and force sensing. In other configurations, a subsent of the cores could be used for both shape sensing and force sensing. In yet other configurations, the cores used for shape sensing can comprise shape sensing triplets or other sensors at different longitudinal areas of the core.

As seen above, since Eq. (7) is a linear equation, the force and the temperature change will linearly shift all four FBG wavelengths and the force and temperature are then expressed as $$F_i = \sum_{j=1}^{4} A_{ij}\Delta\lambda_j \quad (8)$$

where $A_{ij}$, i, j=1, 2, 3, 4 represent the sixteen coefficients related to the mechanical assembly and material strengths that can be determined by experiments; $\Delta\lambda_i$, i=1, 2, 3, 4 indicate the four shifts of Bragg wavelengths, respectively; $F_i$, i=1, 2, 3 represents three components of force, $F_4$ is the temperature change. The amplitude and the direction angles of the force are expressed as $$\begin{cases} F = \sqrt{F_1^2 + F_2^2 + F_3^2} \\ \theta = \cos^{-1}(F_1/F) \\ \gamma = \cos^{-1}(F_2/F) \\ \Delta T = F_4 \end{cases} \quad (9)$$

where $F_1$, $F_2$ and $F_3$ are the three components of the force, $\theta$ and $\gamma$ are the direction angles of the force, respectively. When a computer controlled optical switch makes a scan from channel 1 to 4 acquiring the Bragg wavelength shifts, the applied force and temperature change are achieved from Eq. (9). In another embodiment, a computer controlled optical switch makes a scan from channel 1 to 7 acquiring the Bragg wavelength shifts, the applied force and temperature change are achieved from Eq. (9).

Figure 2:
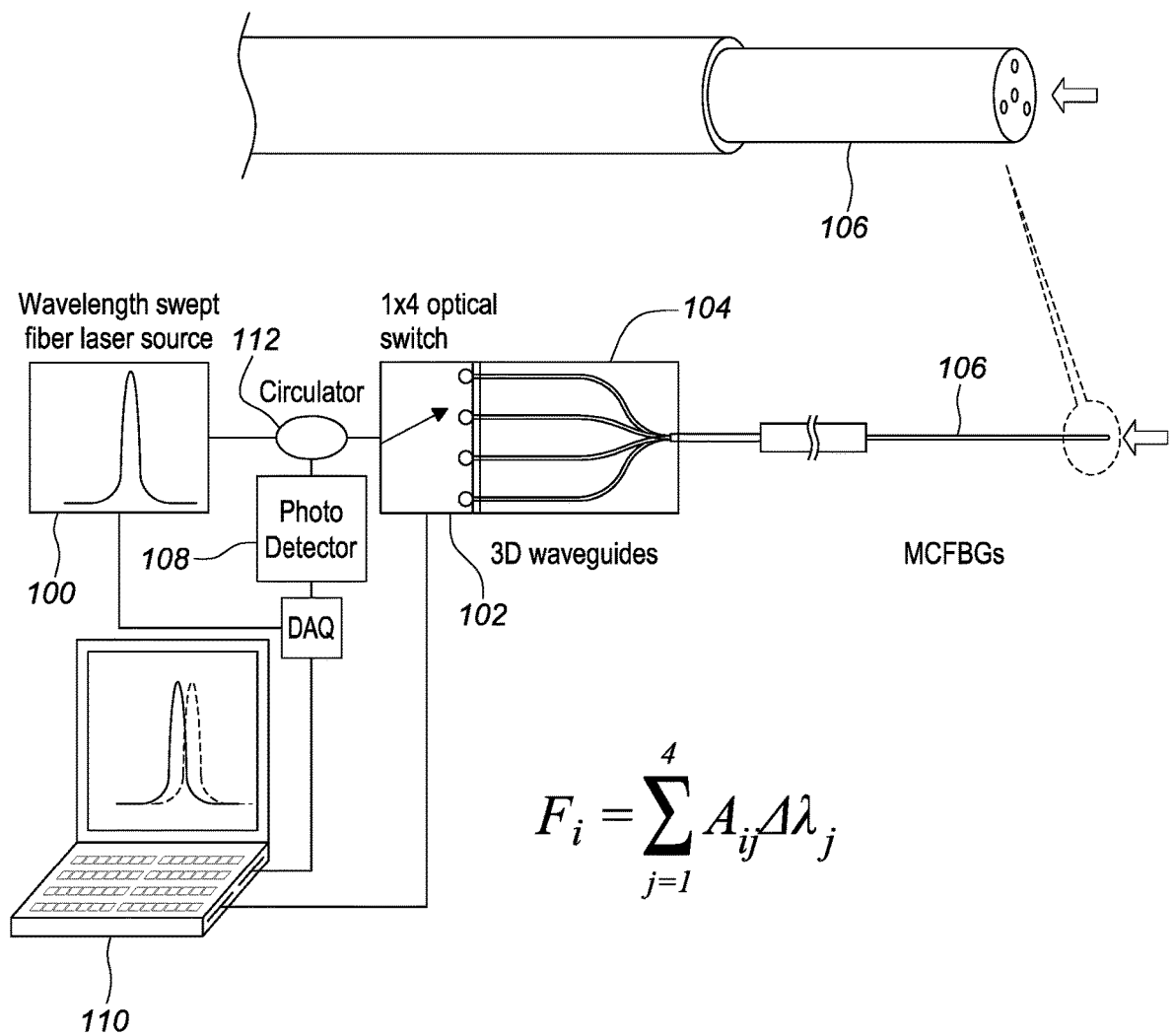
FIG. 2 is a diagrammatic view of one embodiment of a force sensing system.

FIG. 2 is a diagram of a representative force sensing system utilizing a wavelength swept fiber laser source 100, an optical switch 102, a 3D waveguide 104, a computer 110, a photo detector 108, a circulator 112, and a multi-core fiber Bragg gratings 106. In one embodiment, the 3D waveguide can comprise a fiber fan-out. Further, in one embodiment, the computer 110 can comprise a microprocessor. The computer can control the wavelength swept fiber laser source 100 to emit an electromagnetic source or other signal. In the illustrated embodiment, the wavelength swept fiber laser source 100 can transmit the source signal to the circulator 112. The source signal can then pass through the optical switch 102, pass through the 3D waveguide 104, and travel from a proximal end to a more distal portion of the multi-core fiber Bragg gratings 106. A portion of the signal can then be reflected and/or refracted towards the proximal end of the multi-core fiber Bragg gratings 106, through the circulator 112 and to the photo detector 108. In one embodiment, the photo detector 108 can send a signal to the computer 110. The computer can then process the signal to determine a degree of deflection enacted on a distal end of the multi-core fiber Bragg gratings 106 as described herein. In another embodiment, the signal returning from the multi-core fiber Bragg gratings can be directed to a sensor coupled to or part of the computer. While the multi-core fiber Bragg gratings is illustrated separately in the illustrated embodiment, the multi-core fiber Bragg gratings can be placed within a medical device or other object as described throughout this application. In one embodiment, the multi-core fiber can comprise a spun multi-core fiber. In a spun multi-core fiber, the cores of the multi-core fiber can twist throughout a length of the fiber. In some embodiments, a coordinate frame of the multi-core fiber can be synchronized with another two dimensional or three dimensional coordinate frame. Synchronizing the coordinate frames can allow for information acquired in the multi-core fiber coordinate frame to be overlaid on additional coordinate frames.

Representative embodiments and variations using techniques described herein are now described for purposes of example and illustration. An embodiment of a medical catheter with a force-sensing capability may provide, for example, a distal diagnostic or therapeutic tip region which is to be juxtaposed against tissue with a force, an intermediate and more proximal extended flexible lumen, a most proximal control handle with which to manipulate the catheter lumen and tip region within a patient's body lumens or organs, a force sensor to sense one or both of a tip bending force and a tip axial force as the distal tip is contacted to a patient's tissue (e.g., cardiac tissue). In such an embodiment, the force sensor may comprise a combination of a force-displacement calibrated spring and two or more optical displacement sensors capable of reporting one or more deflections of the spring as force is applied to the tip, where the optical displacement sensors comprise two or more Bragg gratings written upon two or more cores of a multi-core optical fiber, and where the detected spring deflections permit the tip force to be computed and reported since the spring is calibrated for force versus deflection and deflection is known.

In further variations and alternatives, the optical displacement Bragg sensors may utilize wavelength scanning to determine displacement, where the wavelength scanning takes place in, for example, a console into which the catheter is connected, or in the handle of the catheter. Another option is for the multi-core fiber to have at least two cores peripheral to the fiber outer diameter, where in a more particular example the multiple cores are angularly distributed about the fiber's central axis in an approximately equally spaced manner. Another option is for the multi-core optical fiber to be optically connected to separate fibers using a 3D optical waveguides, which may further involve mounting an optical connector in or on the supporting or control console into which the catheter is plugged. In another embodiment, the calibrated spring includes a tubular multi-core fiber-encapsulating member whose spring stiffness includes the enclosed fiber. In another embodiment, the calibrated spring includes a separate spring which operates mechanically in parallel to any spring action provided by the fiber or its containment means, the overall net spring being the simultaneous combination of both springs in parallel. In yet another embodiment, the calibrated spring is separate from the fiber or its immediate encapsulation member, and the spring provides all of the calibrated spring action employed in force computation. Still another variation involves pre-stretching the fiber in tension or pre-compressing the fiber in compression during manufacture whether or not the fiber is itself encapsulated. Another variation includes a temperature measurement sensor to correct a Bragg grating detected displacement for thermal expansion, where in an even more particular embodiment the temperature sensor is any one of i) a thermocouple, ii) a thermistor, iii) a Bragg grating whose thermal expansion can be deduced optically and thereby acts as a temperature sensor. Yet another variation of such a medical device positions two or more such Bragg gratings on two or more cores of the fiber, where the gratings have the same axial fiber positions. Alternatively, two or more such Bragg gratings are positioned on a single core of the fiber and have different axial fiber positions. In another example, two or more Bragg gratings on one or more cores may have substantially the same grating period, or may have different grating periods. In one embodiment of the catheter, a region of the multi-core fiber which contains one or more Bragg gratings retains the fiber cladding, where in another embodiment the fiber cladding is stripped therefrom.

In yet another example, the spring allows for at least one of a combined tip bending and tip axial compression, tip bending only, or axial compression only, where in a more specific embodiment the two or more Bragg optical displacement sensors detect at least a component of one or more of a bending force and an axial force. In yet another example, the net force or force component is reported as a vector. Representative variations of the catheter tip include the catheter tip being capable of ablating tissue using a tissue heating or cooling method, the catheter tip being capable of electrically pacing tissue, and the catheter tip being capable of electrically sensing tissue electrical waveforms. In one embodiment, the force information may be displayed on a screen in any numeric, icon or vector form; as an indication that a minimum recommended force has been or has not been attained or has or has-not been maintained, or is used in combination with the time of exposure to the therapy such that a numeric product or index of force and time or force/time integral can be reported. In other variations, the multi-core fiber is designed to prevent fiber buckling. In one embodiment, one or more optical displacement sensors are at least one of (a) immersed in flowed irrigant (e.g., saline) and in direct contact with the irrigant/fluid; (b) immersed in flowed irrigant but isolated from the irrigant by an overlying, encapsulating or encasing member or coating; (c) immersed in flowed irrigant but thermally insulated or buffered from the irrigant by an overlying encapsulating or encasing member or coating having a preselected thermal conductivity; (d) immersed in air, a gas or a vacuum; (e) immersed in a deformable gel; (f) mounted in a groove or channel; (g) cast or molded into a surrounding polymeric containing member. In yet another embodiment, the multi-core optical fiber is also employed with additional Bragg gratings arranged in the intermediate flexible lumen such that the flexing shape of the lumen itself can also be tracked in addition to the tip force. In another embodiment, the multi-core fiber is also employed to perform optical lesion feedback or optical tissue analysis. In some embodiments, the temperature can be measured or frequently updated by holding the catheter in the blood without applied force. Another option involves using a particular core's FBG (e.g., the center FBG) as a reference as bending will not shift the center FBG wavelength. FBGs on three-core or more can be used to measure the force and temperature in one embodiment, where alternatives include: (a) doping one or more of the cores (e.g., the center core) with a different material than other cores to optimize the parameters to separate the Bragg wavelength shifts of the applied force from the temperature to improve the force and temperature sensitivities; (b) making one or more of the cores a different diameter (e.g., the center core) to optimize the parameters to improve the force and temperature sensitivities; (c) where the cladding of the multi-core fiber is optionally designed with holes to optimize the parameters to improve the force and temperature sensitivities; and (d) where FBGs on multi-core crystal fibers are used as a sensor to improve the force and temperature sensitivities.

In addition to providing force sensing functionality, other features may be included with such medical devices to provide further value for physicians during interventional or surgical medical procedures. For example, it would be beneficial to visually perceive relevant portions of the medical device that are otherwise veiled by the patient's body, such as a catheter shaft when introduced into the body and no longer directly visible. The present disclosure provides solutions to such challenges, by providing manners for tracking and mirroring the shape of some or all of the veiled portion of the medical device, such as some or all of the proximal portion and optionally some or substantially all of the distal portion of a catheter shaft during a medical procedure (e.g., during catheter-based diagnosis and/or treatment of tissue).

In one embodiment, both optical force sensing and optical shape sensing are provided. One such manner of providing optical force and shape sensing is described in U.S. Pat. No. 8,622,935, which is incorporated herein by reference in its entirety. Optical conduits, such as optical fiber, may be used to transmit light to optical force sensors that detect forces impacting the catheter tip due to varying contact pressures between the catheter tip and body tissue. Other optical conduits may be used to transmit light along a desired length of the catheter shaft equipped with optical sensors, in order to enable the real-time position of the sensed portion of the catheter shaft to be positionally tracked and rendered for simulation of the catheter shaft within the body.

The optical sensors used for sensing the force against tissue and for sensing the changing shape of the catheter may utilize different optical sensing technologies, or a common optical sensing technology. For example, in one embodiment, optical fibers may be equipped with fiber Bragg gratings or other optical sensors to determine deflection of a distal portion of a catheter, which is representative of a magnitude and direction of a force bearing upon the catheter tip when contacting tissue during a medical procedure. In the same or other optical fibers, fiber Bragg gratings or other optical sensors may also be employed along a length of the catheter shaft that is tracked in real time as the catheter moves and consequently changes shape during the medical procedure.

In embodiments further described below, the optical fibers used for both force sensing and shape sensing may be provided as multiple cores of a multi-core fiber. The multi-core fiber thus provides the light pathways and optical sensors for both force and shape sensing technologies.

Figure 3A:
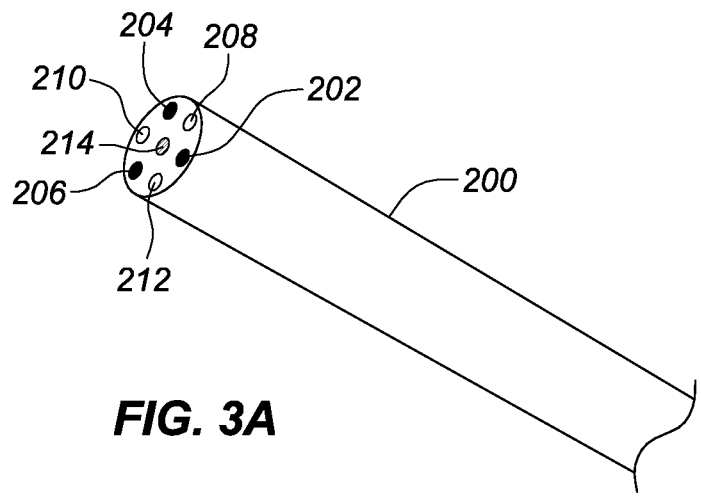
FIGS. 3A and 3B are an isometric views of another embodiment of a multi-core fiber.
Figure 3B:
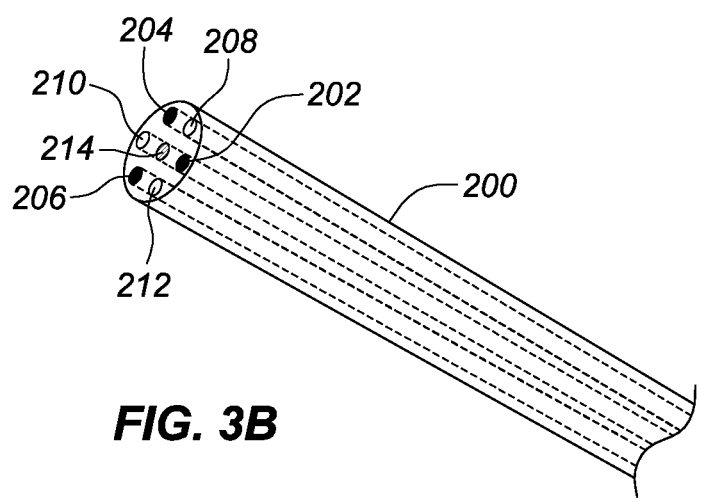
Figure 3C:
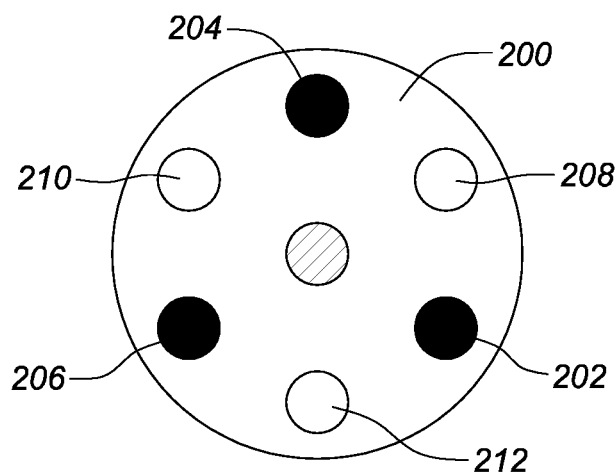
FIG. 3C is an end view of the multi-core fiber of FIGS. 3A and 3B.

One embodiment of a multi-core fiber accommodating both sensors for force sensing and shape sensing is depicted in FIG. 3A. FIG. 3A depicts an isometric view of a multi-core fiber 200. The multi-core fiber 200 can comprise a plurality of separate cores. In the illustrated embodiment, the multi-core fiber 200 can comprise three cores to provide optical conduits for three respective force sensors (not shown). The multi-core fiber 200 can comprise a first optical core 202, a second optical core 204, and a third optical core 206. The multi-core fiber 200 can further comprise a first shape sensing core 208, a second shape sensing core 210, and a third shape sensing core 212 to provide optical conduits for three respective shape sensing sensors (not shown). In the illustrated embodiment, a particular core located anywhere within the fiber, which in one embodiment is the central core 214, may be used to sense temperature changes by way of an optical sensor (e.g., FBG) at a distal core section. Sensing temperature with the central core 214 allows temperature compensation for the remaining off-axis cores 202-212. In other embodiments, four fibers can be used to derive a force component and a temperature. In one embodiment, a temperature peak and a normal peak can both be determined in the same gradient. In another embodiment, a temperature peak and a normal peak can both be determined in the same gradient and at the same magnitude. FIG. 3B depicts an isometric view of the multi-core fiber 200 of FIG. 3A, while also illustrating an extension of the cores 202-214 through the body of the multi-core fiber 200. In one embodiment, a distal end of the multi-core fiber may be melted into a ball-like shape to minimize reflection. FIG. 3C depicts an end view of the multi-core fiber 200 illustrated in FIGS. 3A and 3B and depicts a representative arrangement of the multiple cores 202-212 of fiber 200 from a perspective perpendicular to a longitudinal axis of the fiber 200.

In one embodiment, only shape sensing cores are implemented, such that only the first shape sensing core 208, the second shape sensing core 210, and the third shape sensing core 212, and optionally an additional core 214 (centrally located or not centrally located), are provided in the multi-core fiber 200. For example, the cores may be configured as shape sensing cores having a plurality of fiber Bragg gratings along the fiber, and therefore along the catheter shaft in which the fiber is enclosed. One or more temperature sensors may be included in one or more cores of the fiber. In such an embodiment, only shape sensing is performed utilizing the multi-core fiber, versus both shape sensing and force sensing.

In another embodiment, both shape sensing and force sensing are implemented using common cores, such that each core includes both shape sensing and force sensing sensors. For example, the frequency of light can be different in a common core for each of the force and shape sensing gratings respectively, which allows differentiation of the resulting reflections at the sensor signal processing unit.

Figure 4:
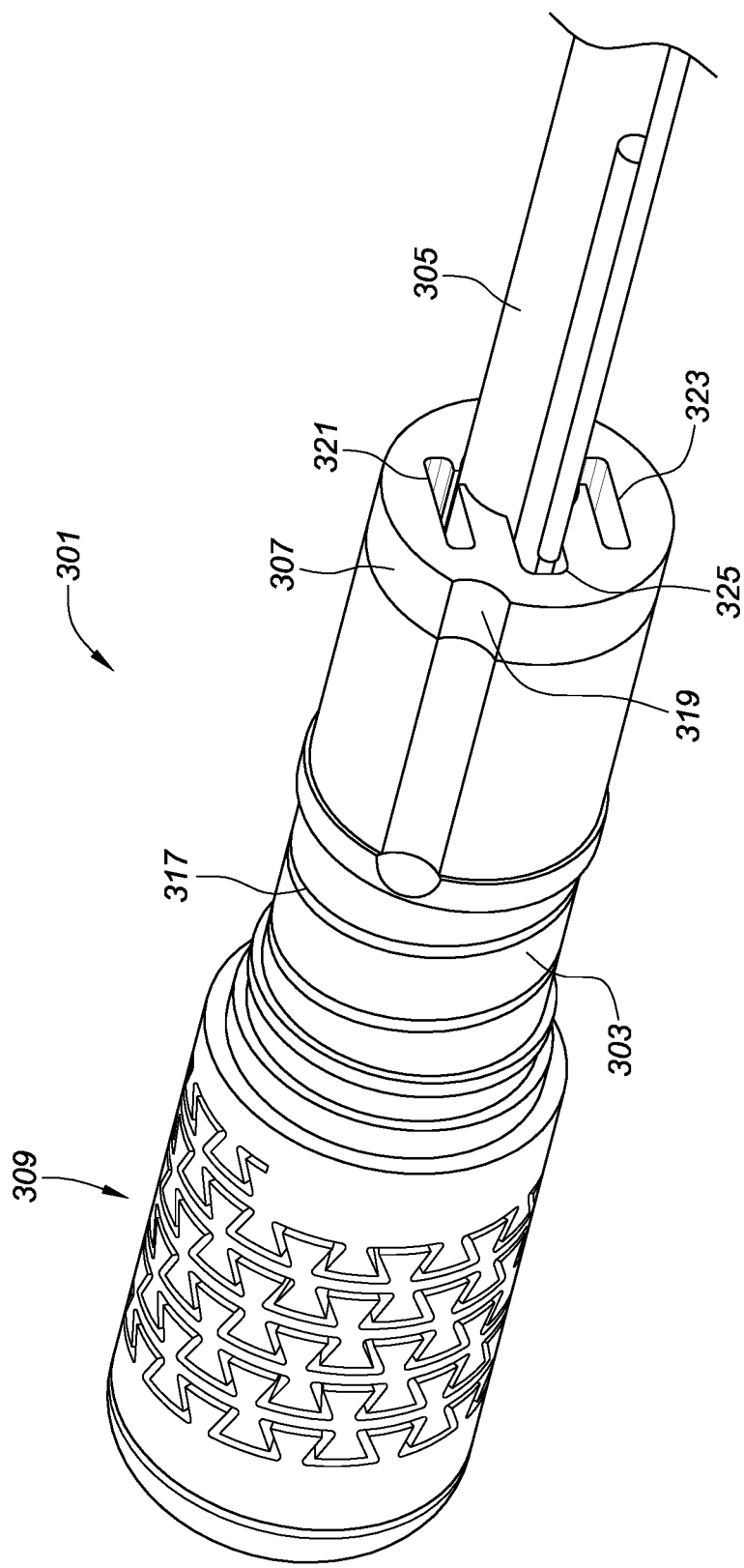
FIG. 4 is an isometric view of one embodiment of a tip assembly comprising a multi-core fiber.

FIG. 4 depicts an isometric view of one embodiment of a tip assembly 301. The tip assembly 301 can comprise a flex tip 309, a force body 303, a fluid cap 307, and an irrigation lumen 305. A multi-core fiber can be disposed within the irrigation lumen 305. In other embodiments, the multi-core fiber can be disposed exterior to the irrigation lumen. The tip assembly 301 can comprise a multi-core fiber that can be disposed within the irrigation lumen 305. The tip assembly 301 can accommodate distal flexing from which at least the force sensors may sense deflection due to force against a structure, such as cardiac tissue. In this embodiment, one or more slots 317 allow the force body 303 to bend due to a force in response to contact with the tissue. For example, where one or more fiber Bragg grating force sensors are within three respective cores and within the force body 303, the force sensors can identify deflection of the force body 303 in response to varying degrees of contact with tissue. In some embodiments, the force body can comprise a coupler. Such sensors based on fiber Bragg grating may be implemented as described herein, and/or as described in U.S. Pat. No. 8,182,433 assigned to the assignee of the instant application, which is incorporated herein by reference in its entirety. In other embodiments, the force sensors associated with the force sensing cores may utilize a different optical technology. The fluid cap 307 can further comprise a shaft electrode groove 319, a first electrical channel 321, a second electrical channel 323, and a central channel 325. The shaft electrode groove 319 can comprise an annular space within an outer wall of the fluid cap 307 configured to allow an electrical wire to pass through the shaft electrode groove 319 to an electrode disposed distal of the fluid cap 307. The first electrical channel 321 and the second electrical channel 323 can comprise gaps disposed adjacent the central channel 325. The first electrical channel 321 and the second electrical channel 323 can be configured to allow for the passage of electrical wires, thermal sensors, anchor wires, and other materials as would be known to one of ordinary skill in the art from a position proximal of the tip assembly 301 to an inner portion of the tip assembly 301.

Figure 5:
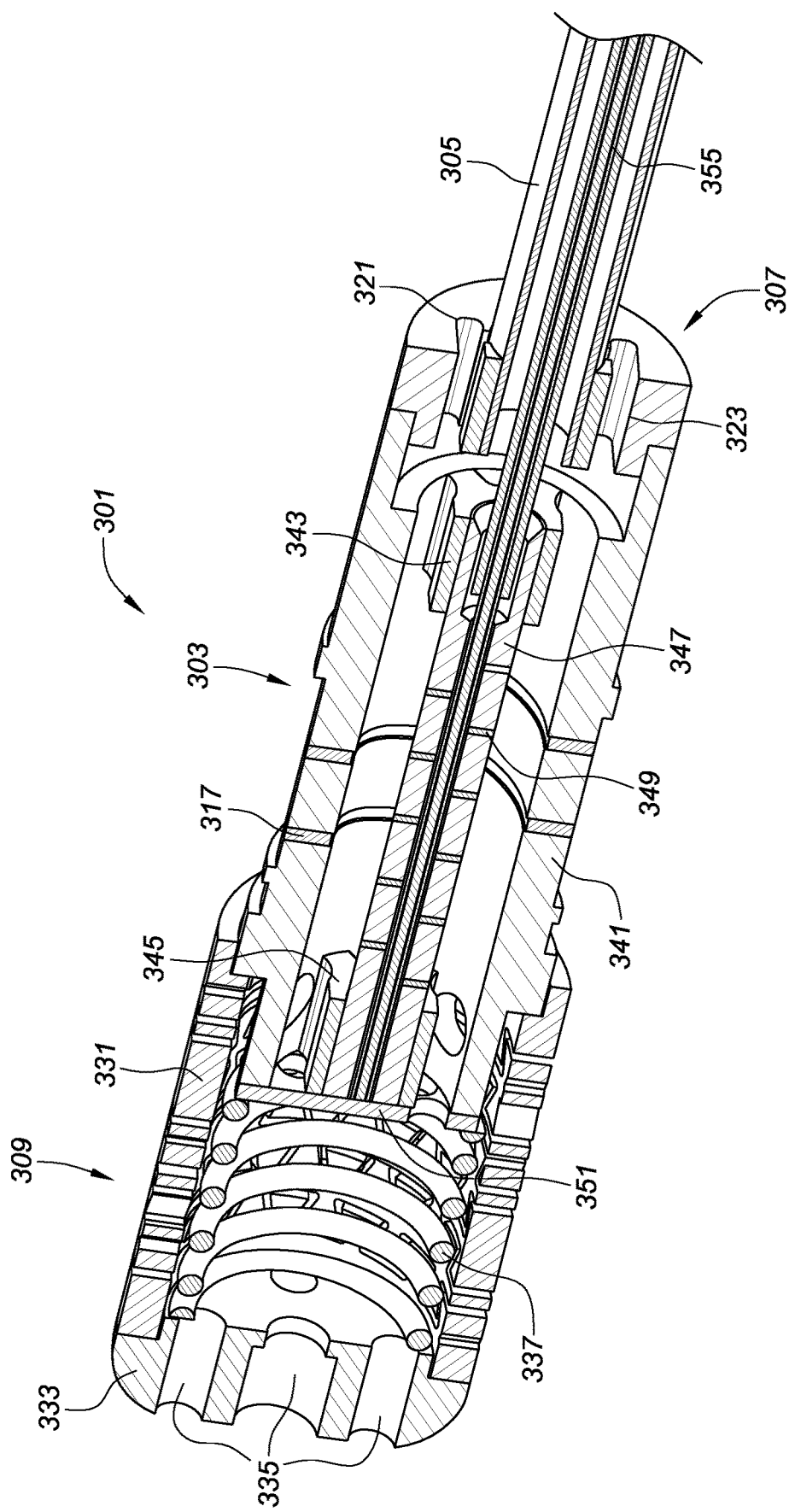
FIG. 5 is an isometric cross-sectional view of the tip assembly of FIG. 4.

FIG. 5 depicts an isometric cross-sectional view of the embodiment of the tip assembly 301 seen in FIG. 4. The tip assembly 301 can comprise a flex tip 309, a force body 303, a fluid cap 307, an irrigation lumen 305, and a multi-core fiber 355. The flex tip 309 can be coupled to a distal end of the force body 303. The flex tip 309 can comprise an electrode for sensing or ablating. The flex tip 309 can further be configured to deliver energy. The flex tip 309 can comprise a spring 337, a flex tip wall 331, and a flex tip cap 333. The spring 337 can be disposed within an interior portion of the flex tip 309 and can be surrounded by the flex tip wall 331. The flex tip cap 333 can comprise a plurality of irrigation through holes 335 and can be coupled to a distal end of the flex tip wall 331. The plurality of irrigation through holes 335 can be configured to allow for an irrigant that is distributed to an inner portion of the flex tip 309 to pass therethrough to an exterior portion of the flex tip 309.

In other embodiments, the tip assembly can comprise a tip electrode. The tip electrode can comprise a flex tip electrode as described herein, or other tip electrodes as would be known to one of ordinary skill in the art. The tip electrode can be configured for sensing or ablating tissue. The force body 303 can comprise a force body outer wall 341, at least one force body slot 317, an irrigation balancing plate 351, a first fiber support tube center 343, and a second fiber support tube center 345. The irrigation balancing plate 351 can be coupled to a distal end of the force body outer wall 341. In the illustrated embodiment, the irrigation balancing plate 351 and the distal portion of the force body outer wall 341 can be disposed within a proximal portion of the flex tip 309. In the illustrated embodiment, the distal portion of the force body 303 can be disposed within an interior portion of the flex tip 309 and surrounded circumferentially by the flex tip wall 331. The at least one force body slot 317 can be a helical slot in the force body outer wall 341. The force body slot 317 can be configured to allow for the force body 303 to flex when force is applied to the force body 303. In the illustrated embodiment, the force body slot 317 can comprise a slot through an entirety of the force body outer wall 341. In other embodiments, the force body slot 317 can comprise a cut or other removal of material through all or part of the force body to allow the force body to bend when pressure is applied to the force body. The force body slot 317 can be filled with a flexible material that conforms to the force body 303. In one embodiment, the flexible material can comprise a water tight seal. The first fiber support tube center 343 and the second fiber support tube center 345 can be coupled to an interior surface of the force body outer wall 341. The first fiber support tube center 343 and the second fiber support tube center 345 can coupled to the multi-core fiber 355 and can secure the multi-core fiber 355 within the force body 303. In other embodiments, the force body can further comprise at least one thermocouple. The at least one thermocouple can be disposed within an interior portion of the force body. In one embodiment, the at least one thermocouple can be disposed within an irrigant pool within the force body. The at least one thermocouple be used to determine a temperature of irrigant within the force body. Further, the temperature of the irrigant can be used to determine a temperature of the multi-core fiber within the force body.

The multi-core fiber 355 can comprise a fiber support tube 347 and a support tube slot 349. The support tube slot 349 can comprise a helical slot in the fiber support tube 347. The support tube slot 349 can be configured to allow for the fiber support tube 347 to flex when force is applied to the force body 303. In the illustrated embodiment, the support tube slot 349 can comprise a slot through an entirety of the fiber support tube 347. In other embodiments, the support tube slot 349 can comprise a cut or other removal of material through all or part of the fiber support tube 347 to allow the force body 303 to bend and/or compress when pressure is applied to the force body 303. The support tube slot 349 can be filled with a flexible material that conforms to the fiber support tube 347. In one embodiment, the flexible material can comprise a water tight seal. The irrigation lumen 305 can comprise a lumen to deliver irrigation to the tip assembly 301. The multi-core fiber 355 can be disposed within an interior portion of the irrigation lumen 305. In one embodiment, a distal end of the irrigation lumen 305 can be coupled to a central channel of the fluid cap 307.

The fluid cap 307 can comprise a first electrical channel 321 and a second electrical channel 323. The fluid cap 307 can be coupled to a proximal end of the force body 303. The first electrical channel 321 and the second electrical channel 323 can comprise channels through the fluid cap 307. Electrical wires, support wires, anchoring members and other devices can be passed through the first electrical channel 321 and the second electrical channel 323 to allow various components access to an interior portion of the tip assembly 301.

Figure 6:
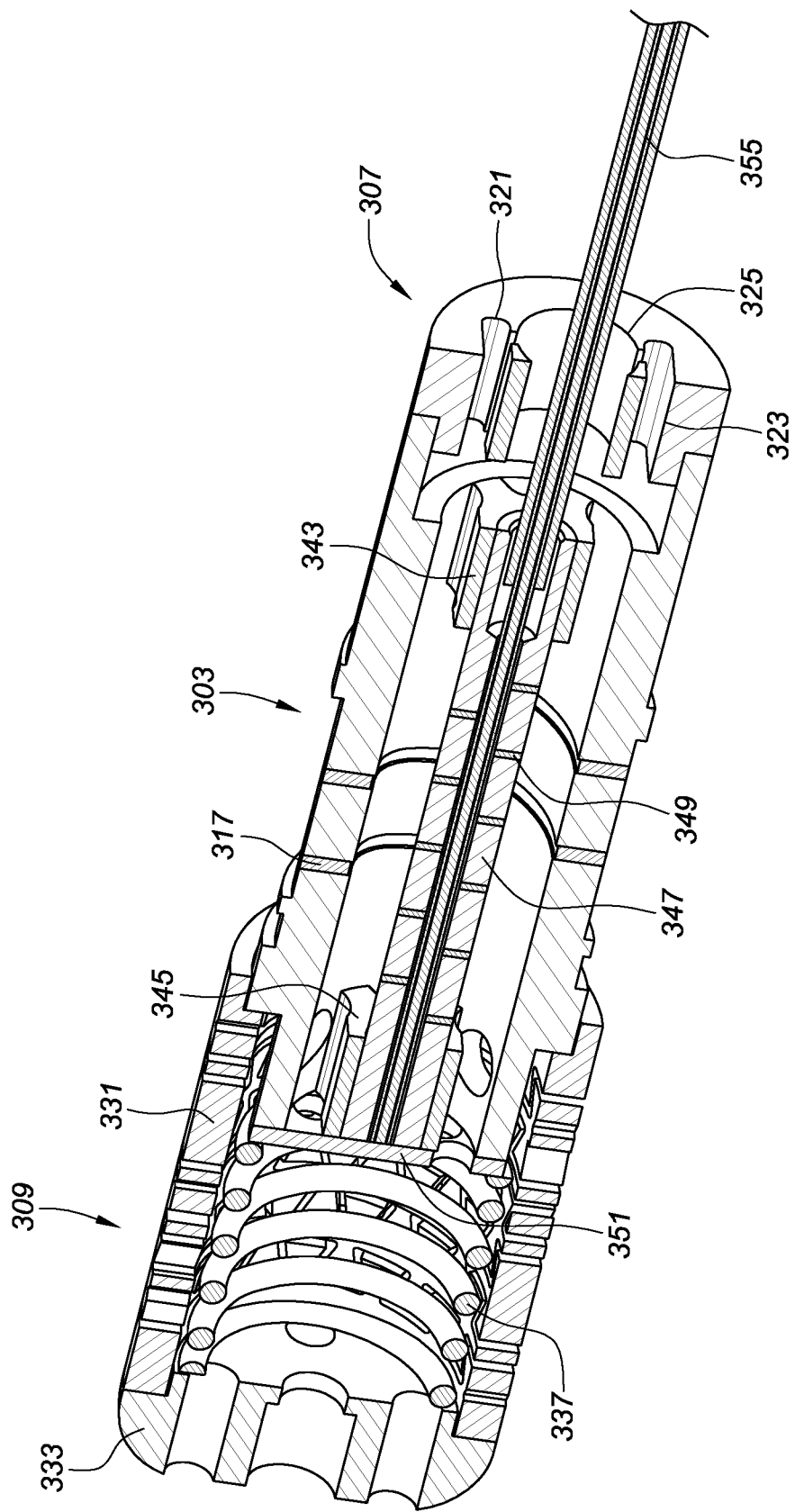
FIG. 6 is an isometric cross-sectional view of the tip assembly of FIGS. 4 and 5.

FIG. 6 illustrates an isometric cross-sectional view of the embodiment of the tip assembly 301 seen in FIGS. 4 and 5. The tip assembly 301 can comprise a flex tip 309, a force body 303, a fluid cap 307, and a multi-core fiber 355. The irrigation lumen as seen in FIG. 5 has been omitted from the drawing to allow for a better view of the multi-core fiber 355 passing through the fluid cap 307. As seen in the illustrated embodiment, the multi-core fiber 355 can pass through a center of the central channel 325 of the fluid cap 307. The multi-core fiber 355 can follow a center-line of the force body 303. The multi-core fiber 355 can be positioned and kept in the center of the force body 303 through the first fiber support tube center 343 and the second fiber support tube center 345.

Figure 7:
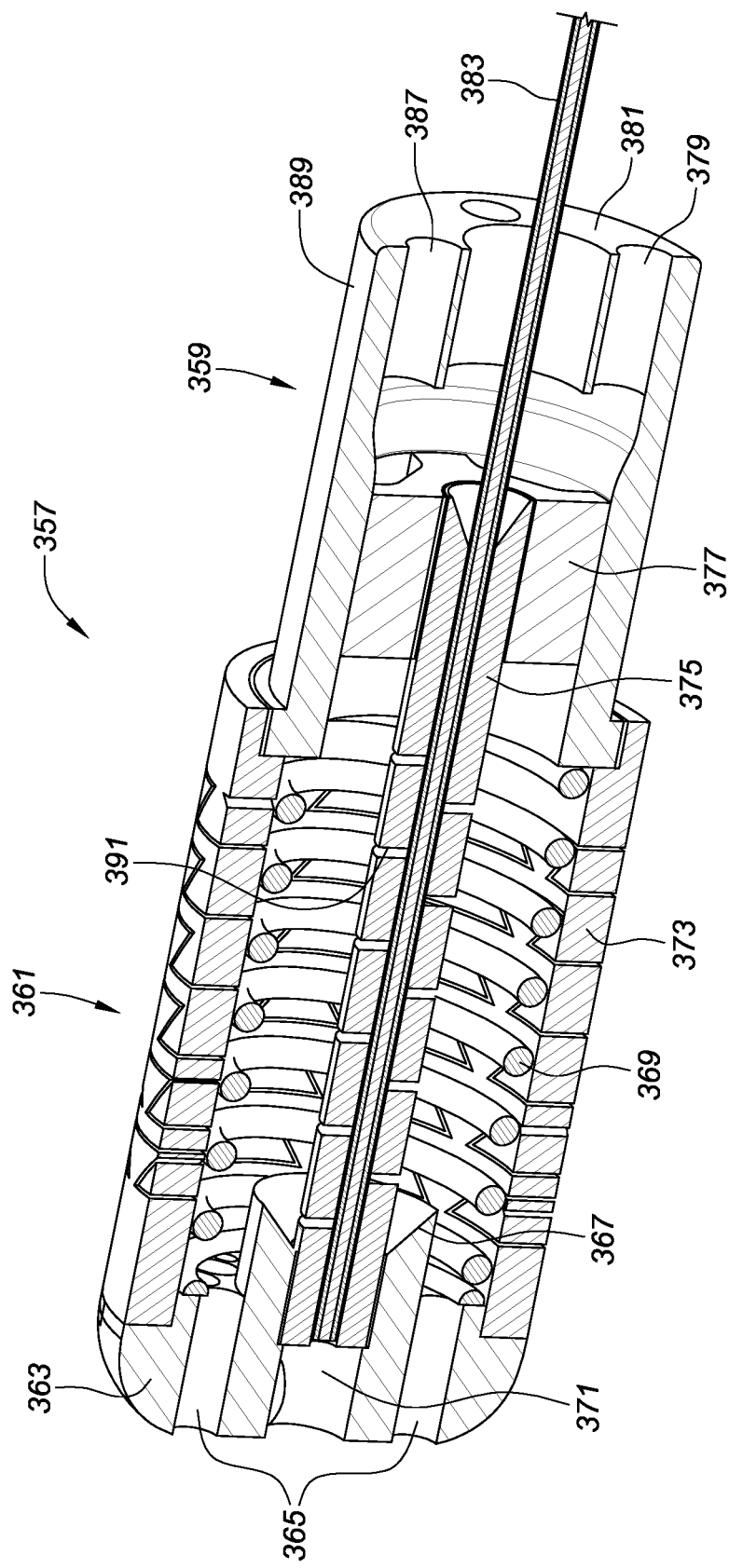
FIG. 7 is an isometric cross-sectional view of one embodiment of a tip assembly.

FIG. 7 depicts an isometric cross-sectional view of another embodiment of a tip assembly 357. The tip assembly 357 can comprise a flex tip 361, a coupler 359, and a multi-core fiber 383. The flex tip 361 can be coupled to a distal end of the coupler 359. The flex tip 361 can comprise an electrode for sensing or ablating. The flex tip 361 can further be configured to deliver energy. The flex tip 361 can comprise a spring 369, a flex tip wall 373, and a flex tip cap 363. The spring 369 can be disposed within an interior portion of the flex tip 361 and can be surrounded by the flex tip wall 373. The flex tip cap 363 can comprise a plurality of irrigation through holes 365 and a second fiber support tube center 367. The flex tip cap 363 can be coupled to a distal end of the flex tip wall 373. The plurality of irrigation through holes 365 can be configured to allow for an irrigant that is distributed to an inner portion of the flex tip 361 to pass therethrough to an exterior portion of the flex tip 361. In the illustrate embodiment, the second fiber support tube center 367 can be integral with the flex tip cap 363. The second fiber support tube center 367 can comprise an inner wall 371. The inner wall can be sized and configured to receive a distal end of a fiber support tube. In other embodiments, the second fiber support tube center 367 can be configured to receive a distal portion a fiber support tube. The second fiber support tube center 367 can be configured to secure the distal end of the fiber support tube to the flex tip cap 363. Through securing the distal end of the fiber support tube, the multi-core fiber can bend as described throughout this application. In other embodiments, the tip assembly can comprise a tip electrode. The tip electrode can comprise a flex tip electrode as described herein, or other tip electrodes as would be known to one of ordinary skill in the art. The tip electrode can be configured for sensing or ablating tissue. The coupler 359 can comprise a coupler outer wall 389, a coupler proximal end 381, and a first fiber support tube center 377. In some embodiments, the coupler can comprise a force body. In the illustrated embodiment, the distal portion of the coupler 359 can be disposed within an interior portion of the flex tip 361 and surrounded circumferentially by the flex tip wall 373. The first fiber support tube center 377 can be coupled to an interior surface of the coupler outer wall 389. The first fiber support tube center 377 and the second fiber support tube center 367 can coupled to the multi-core fiber 383 and can secure the multi-core fiber 383 within the tip assembly 357. In other embodiments, the coupler can further comprise at least one thermocouple. The at least one thermocouple can be disposed within an interior portion of the coupler or within the flex tip. In one embodiment, the at least one thermocouple can be disposed within an irrigant pool within the coupler. The at least one thermocouple be used to determine a temperature of irrigant within the coupler. Further, the temperature of the irrigant can be used to determine a temperature of the multi-core fiber within the coupler.

The multi-core fiber 383 can comprise a fiber support tube 375 and a support tube slot 391. As stated in the rest of the application, the multi-core fiber can comprise a plurality of cores. Each of these cores can be used for one or more of force sensing, shape sensing, or temperature compensation. In various embodiments, each of the cores can be configured to use the force sensing, shape sensing, or temperature compensation at the same time or separately. In the illustrated embodiment, the fiber support tube 375 can be disposed within an interior portion of the flex tip 361. In the illustrated embodiment, a distal portion of the fiber support tube 375 can be coupled to the second fiber support tube center 367. The second fiber support tube center 367 can be integral with the flex tip cap 363. A proximal portion of the fiber support tube 375 can be coupled to the first fiber support tube center 377. In the illustrated embodiment the first fiber support tube center 377 can be disposed within the coupler and the second fiber support tube center 367 can be integral with the flex tip cap 363. The fiber support tube 375 can be disposed within an interior portion of the coupler 359, the flex tip wall 373, and the flex tip cap 363. The support tube slot 391 can comprise a helical slot in the fiber support tube 375. The support tube slot 391 can be configured to allow for the fiber support tube 375 to flex when force is applied to the tip assembly 357. In the illustrated embodiment, the support tube slot 391 can comprise a slot through an entirety of the fiber support tube 375. In other embodiments, the support tube slot 391 can comprise a cut or other removal of material through all or part of the fiber support tube 375 to allow the tip assembly 357 to bend and/or compress when pressure is applied to the tip assembly 357. The support tube slot 391 can be filled with a flexible material that conforms to the fiber support tube 375. In one embodiment, the flexible material can comprise a water tight seal.

The coupler proximal end 381 can comprise a first electrical channel 379 and a second electrical channel 387. The coupler proximal end 381 can be coupled and/or integral to a proximal end of the coupler 359. The first electrical channel 379 and the second electrical channel 387 can comprise channels through the coupler proximal end 381. Electrical wires, support wires, anchoring members and other devices can be passed through the first electrical channel 379 and the second electrical channel 387 to allow various components access to an interior portion of the tip assembly 357.

Figure 8:
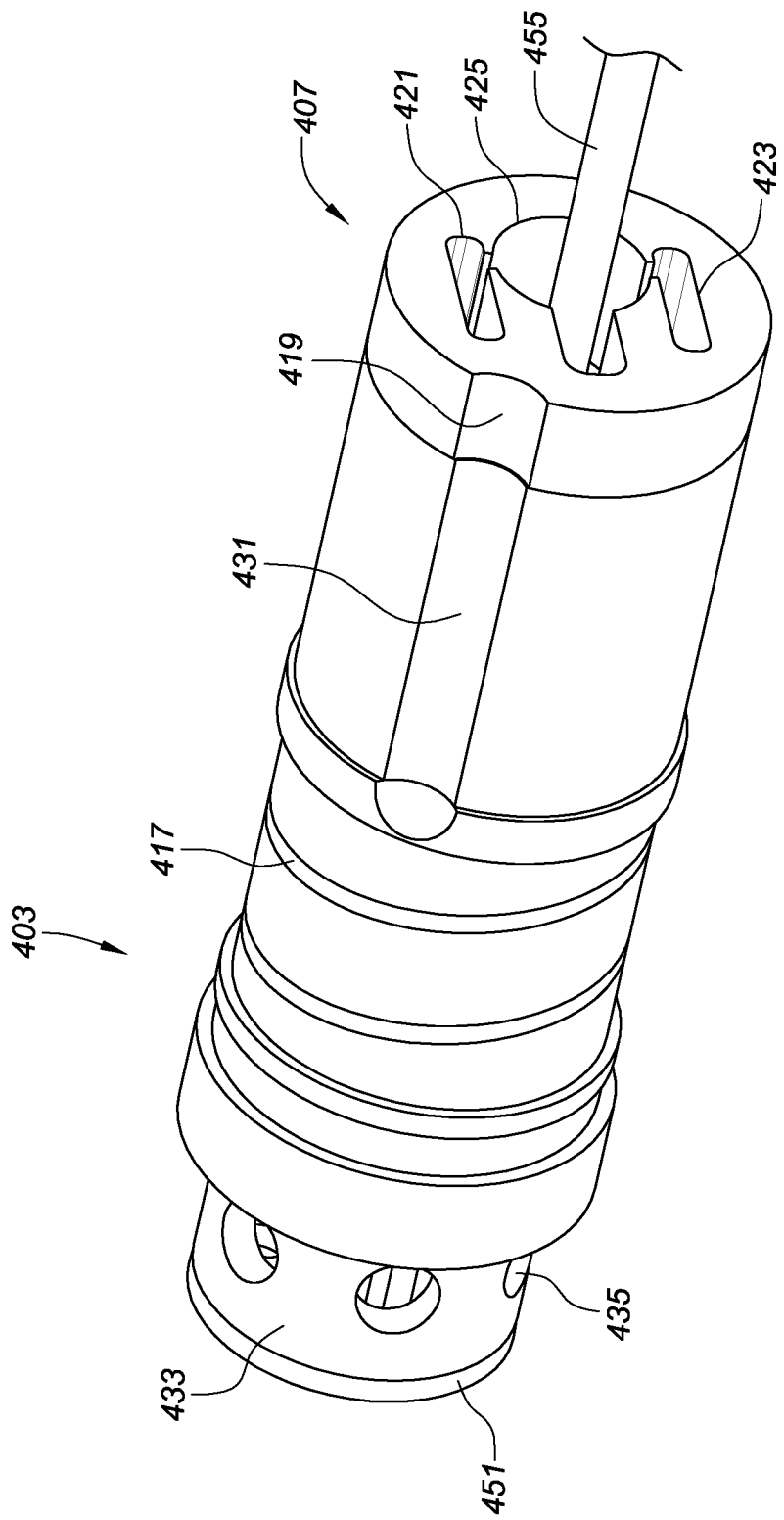
FIG. 8 is an isometric view of one embodiment of a force body, a fluid cap, and a multi-core fiber.

FIG. 8 depicts an isometric view of an embodiment of a force body 403, a fluid cap 407, and a multi-core fiber 455. The force body 403 can comprise an irrigation balancing plate 451, a distal neck 433, at least one force body irrigation port 435, a force body slot 417, and a force body shaft electrode ring groove 431. The irrigation balancing plate 451 can be coupled to a distal end of the distal neck 433 of the force body 403. The at least one force body irritation port 435 can be disposed on the distal neck 433 of the force body 403. The at least one force body irrigation port 435 can be configured to allow irrigant to pass from an inner portion of the force body 403 to an exterior portion of the force body 403. In the illustrated embodiment, the at least one force body irrigation port 435 can comprise a plurality of irrigation ports that can be evenly distributed around a circumference of the distal neck 433. In other embodiments, the at least one force body irrigation port can comprise a plurality of irrigation ports that can be distributed in an uneven configuration. The uneven configuration can be configured to direct more irrigant to certain areas of the tip electrode. The increased irrigant can be used to cool certain portions of the tip electrode or to push additional irrigant to an area external of the tip electrode when compared to areas of the tip electrode without a force body irrigation port adjacent. The force body shaft electrode ring groove 431 can comprise a depression within an exterior wall of the force body 403. The force body shaft electrode ring groove 431 can comprise a longitudinal groove or depression within the force body 403. The force body shaft electrode ring groove 431 can be disposed between a proximal end of force body 403 and a more distal position. The force body shaft electrode ring groove 431 can be configured to allow an electrical wire to be disposed therein. The force body shaft electrode ring groove 431 can further be configured to allow for the electrical wire to terminate and/or couple to a ring electrode disposed adjacent to the force body 403. The fluid cap 407 can comprise a central channel 425, a first electrical channel 421, a second electrical channel 423, and a cap shaft electrode ring groove 419. The cap shaft electrode ring groove 419 can comprise a depression within an exterior wall of the fluid cap 407. The cap shaft electrode ring groove 419 can comprise a longitudinal groove or depression within the fluid cap 407. The cap shaft electrode ring groove 419 can be disposed between a proximal end of fluid cap 407 and a distal end of the fluid cap 407. The cap shaft electrode ring groove 417 can be configured to allow an electrical wire to be disposed therein.

Figure 9:
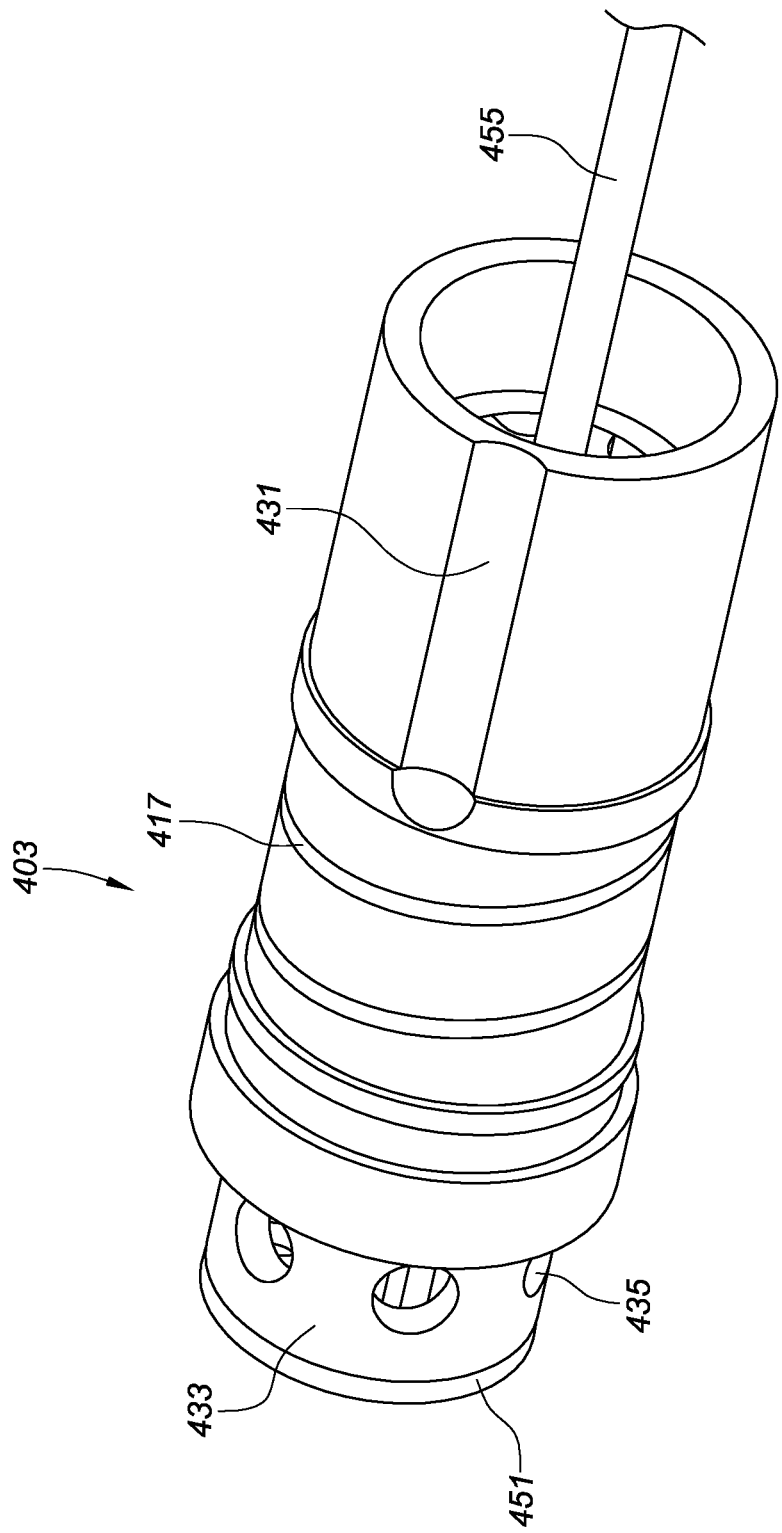
FIG. 9 is an isometric view of the force body and the multi-core fiber of FIG. 8.

FIG. 9 depicts an isometric view of the embodiment of the force body 403 and the multi-core fiber 455 illustrated in FIG. 8. In the illustrated embodiment, the fluid cap has been removed and is not shown. The force body 403 can comprise an irrigation balancing plate 451, a distal neck 433, at least one force body irrigation port 435, a force body slot 417, and a force body shaft electrode ring groove 431.

Figure 10:
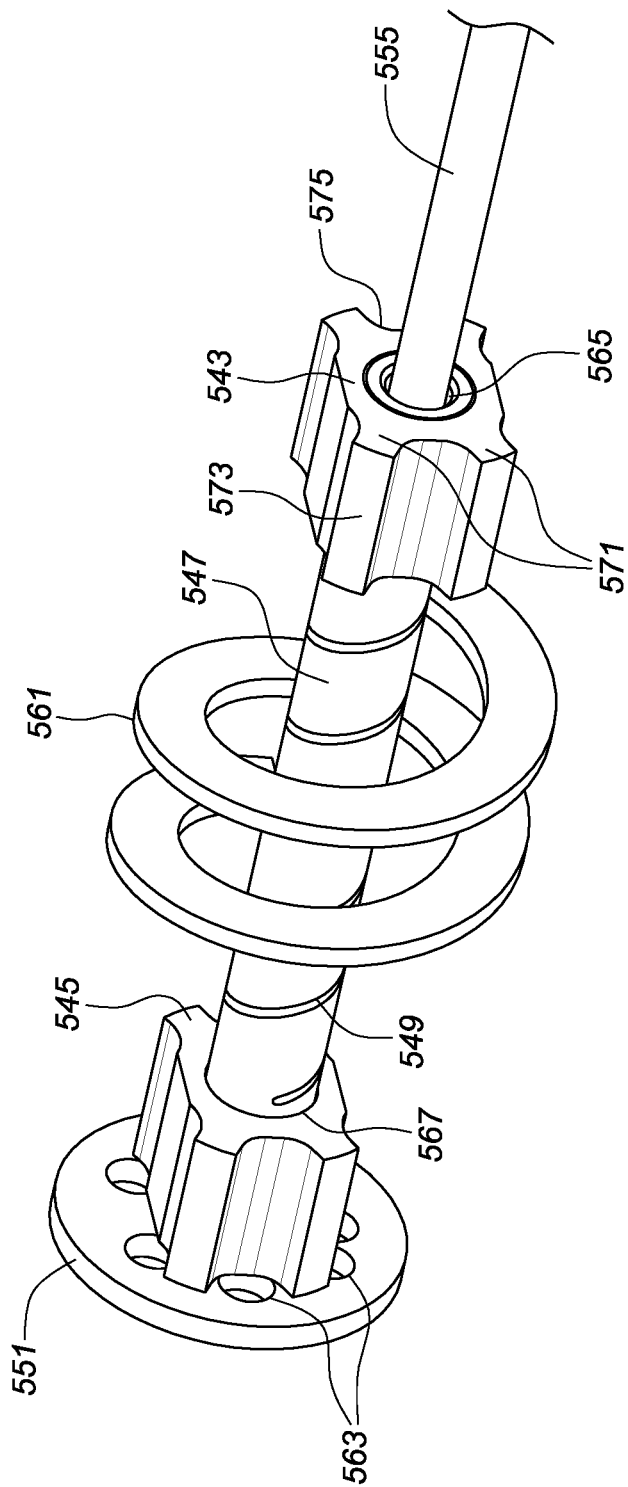
FIG. 10 is an isometric view of some components of an embodiment of a force body.

FIG. 10 depicts an isometric view of some components of a force body. FIG. 10 depicts an irrigation balancing plate 551, a first fiber support tube center 543, a second fiber support tube center 545, a support tube 547, a support tube slot 549, a force body sealant 561, and a multi-core fiber 555. The irrigation balancing plate 551 can comprise at least one plate irrigation through holes 563. The at least one plate irrigation through holes 563 can be configured to allow an irrigant to pass from a proximal side of the irrigation balancing plate 551 to a distal side of the irrigation balancing plate 551. The first fiber support tube center 543 can comprise a first center through-hole 565 and the second fiber support tube center 545 can comprise a second center through-hole 567. The multi-core fiber 555 can comprise a support tube 547 and a support tube slot 59. The support tube 547 can surround a distal portion of the multi-core fiber 555. The force body sealant 561 can comprise a sealant formed in a helical pattern that can fit within the force body slot described throughout this application. The force body sealant 561 can surround a distal portion of the multi-core fiber 555. A distal end of the support tube 547 can be coupled to and disposed within the second through hole 567 of the second fiber support tube center 545 and a proximal end of the support tube 547 can be coupled to and disposed within the first through hole 565 of the first fiber support tube center 543.

The first fiber support tube center 543 and the second fiber support tube center 545 can each further comprise at least one centering protrusion 571. Each of the ate least one centering protrusion 571 can extend outward in a radial direction from a center of the fiber support tube center. Each of the ate least one centering protrusion 571 can comprise a protrusion outer surface 573. The protrusion outer surface 573 can be shaped and configured to interact with an inner wall of a force body. The protrusion outer surface can interact with the inner wall of the force body to center the through-hole in the force body. In the illustrated embodiment, each of the fiber support tube centers can comprise four centering protrusions. In one embodiment, each of the centering protrusions can be spaced 90 degrees from each neighboring centering protrusion. In the illustrated embodiment, the centering protrusions are spaced to create a rectangular shape by their outer surface. In the illustrated embodiment, each of the fiber support tube centers further comprises a centering depression 575 between each of the at least one centering protrusion 571. Each fiber support tube center can comprise multiple centering depressions 575. In one embodiment, at least one of the centering depressions can be configured to allow for electrical wires or other components of a catheter to pass through the centering depression and proceed to a more distal location within the tip assembly.

Figure 11:
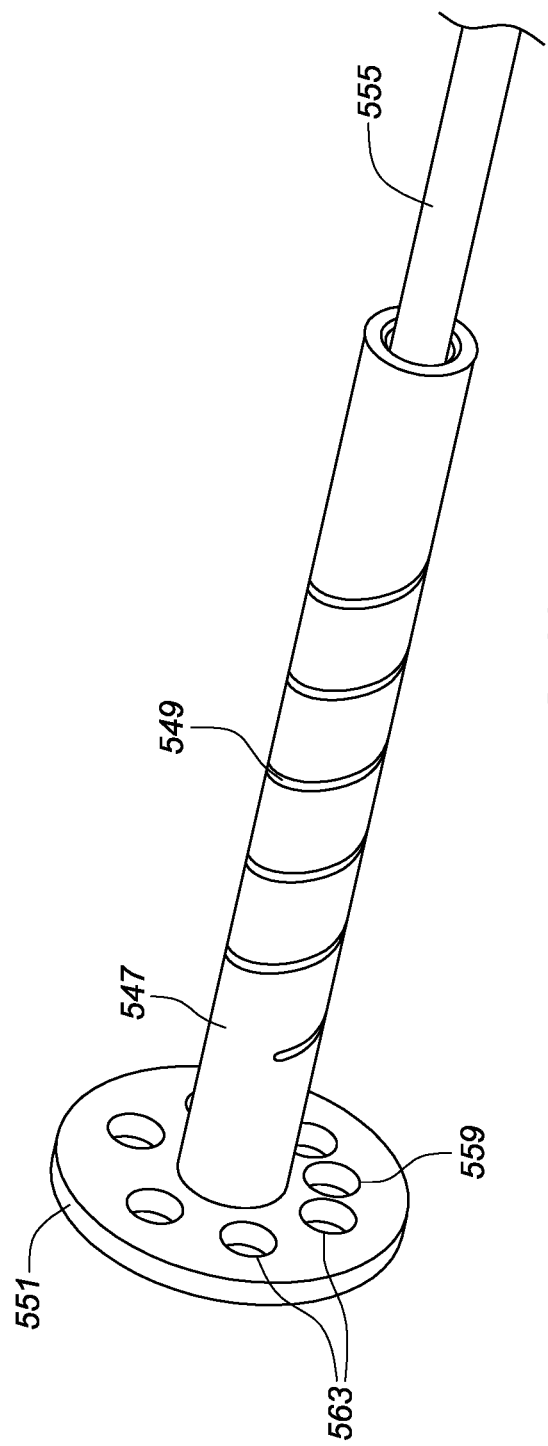
FIG. 11 is an isometric view of some components of the force body of FIG. 10.

FIG. 11 depicts an isometric view of some of the components illustrated in FIG. 10. FIG. 11 depicts an irrigation balancing plate 551, a support tube 547, a support tube slot 549, a thermocouple through hole 559, and a multi-core fiber 555. In the illustrated embodiment, a longitudinal axis of the multi-core fiber 555 passes through a center portion of the irrigation balancing plate 551. Further, in the illustrated embodiment, the at least one plate irrigation through holes 563 comprise a plurality of plate irrigation through holes. The plurality of plate irrigation through holes can be distributed evenly around a circumference of the irrigation balancing plate 551. In other embodiments, the plurality of plate irrigation through holes can comprise various distances between each other as would be desired to direct fluid into a catheter tip. In the illustrated embodiment, the plurality of plate irrigation through holes can be the same distance from a center point of the irrigation plate. In other embodiments, the plurality of plate irrigation through holes can vary in distance from a center point of the irrigation plate. The thermocouple through hole 559 can be used to pass a thermocouple from proximal of the irrigation balancing plate 551 to a more distal portion of the tip assembly. In another embodiment, the thermocouple through hole can be used and/or configured to pass a thermal sensor from proximal of the irrigation balancing plate 551 to a more distal portion of the tip assembly. In other embodiments, the irrigation balancing plate 551 can comprise a plurality of thermocouple through holes. In yet another embodiment, the thermocouple through hole can be sized and configured to pass multiple thermocouples or other thermal sensors through the irrigation balancing plate.

Figure 12:
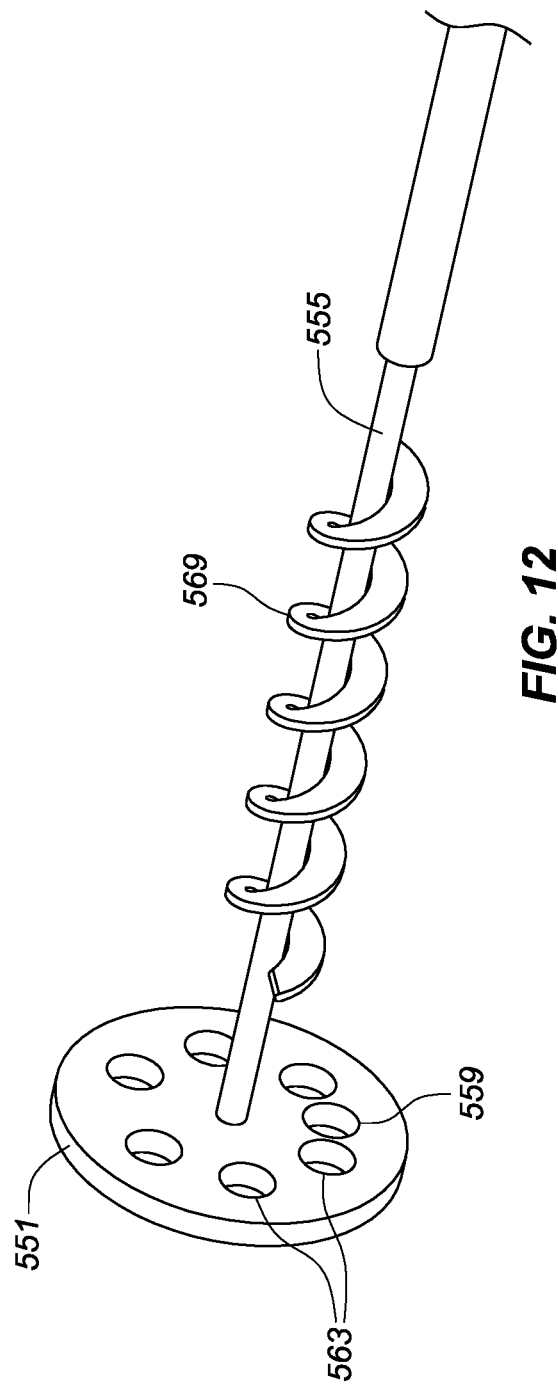
FIG. 12 is an isometric view of some components of the force body of FIGS. 10 and 11.

FIG. 12 depicts an isometric view of some of the components illustrated in FIGS. 10 and 11. FIG. 12 depicts an irrigation balancing plate 551, a multi-core fiber 555, a fiber sealant 569, a thermocouple through hole 559, and at least one plate irrigation through hole 563. The fiber sealant 569 can surround a distal portion of the multi-core fiber 555. The fiber sealant 569 can be formed in a helical shape surrounding the multi-core fiber 555. The fiber sealant 569 can be configured to allow the multi-core fiber 555 and support tube to move when a lateral or vertical force is imparted to the multi-core fiber 555.

Figure 13:
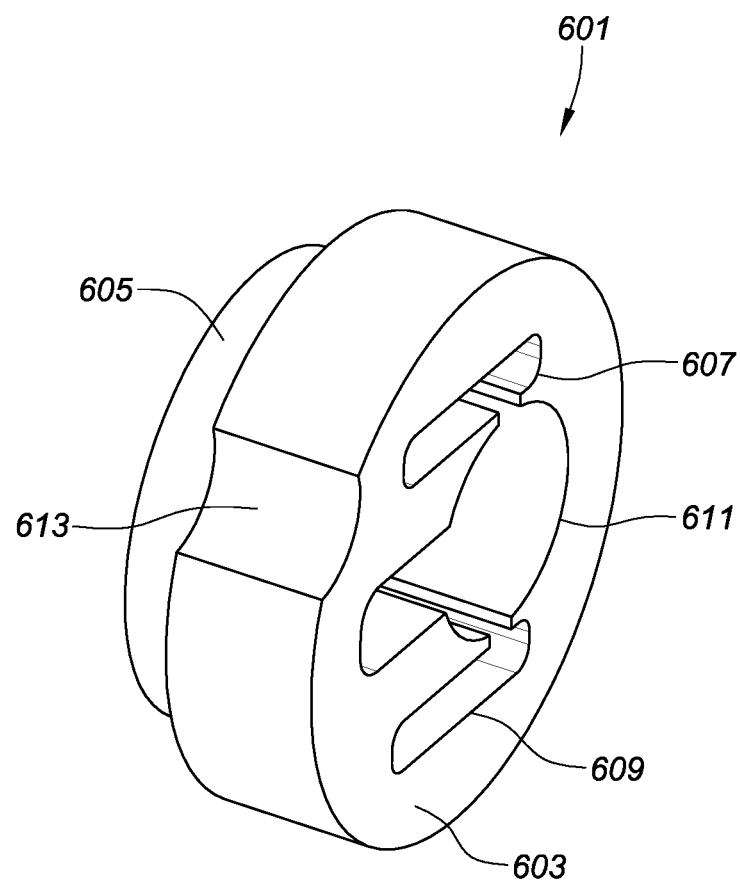
FIG. 13 is an isometric view of one embodiment of a fluid cap.

FIG. 13 depicts an isometric view of an embodiment of a fluid cap 601. The fluid cap 601 can comprise a shaft electrode ring groove 613, a first electrical channel 607, a second electrical channel 609, a center channel 611, a proximal face 603, and a distal portion 605. The distal portion 65 of the fluid cap 601 can comprise a smaller diameter than a more proximal portion of the fluid cap 601. The distal portion 605 can be configured to couple to another component. In one embodiment, the distal portion 605 can be configured to couple to a force body. The central channel 611 can be configured to couple to an irrigation lumen. The first electrical channel 607 and the second electrical channel 609 can each comprise a cavity that extends from the proximal face 603 of the fluid cap 601 to a distal end of the fluid cap 601. Each of the first electrical channel 607 and the second electrical channel 609 can be configured to allow for electrical wires or other components of a catheter to pass through the fluid cap 601.

Figure 14:
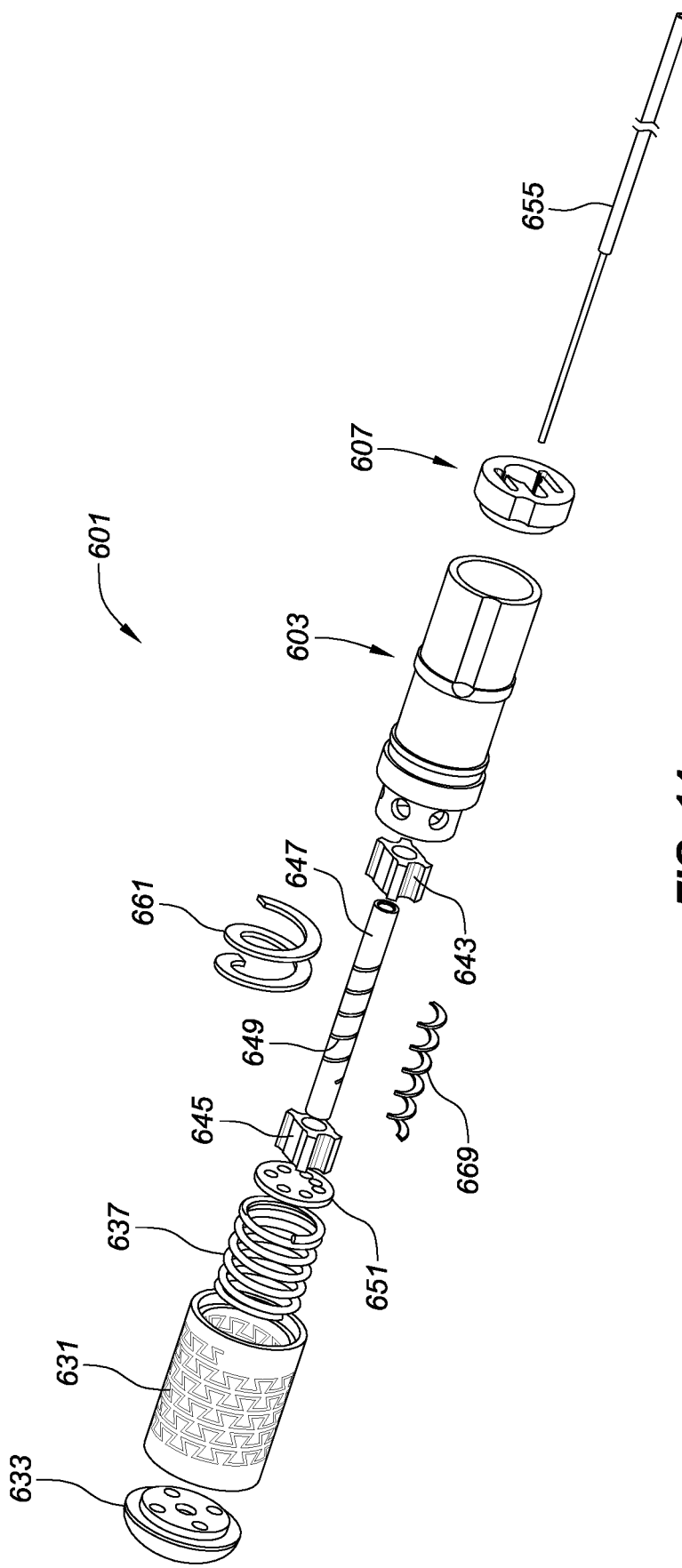
FIG. 14 is an isometric, blow out view of one embodiment of a tip assembly comprising a multi-core fiber.

FIG. 14 depicts an isometric blown out view of one embodiment of a tip assembly 601. The tip assembly 601 comprises a flex tip cap 633, a flex tip wall 631, a spring 637, an irrigation balancing plate 651, a second fiber support tube center 645, a support tube 647, a support tube slot 649, a support tube sealant 669, a first fiber support tube center 643, a force body 603, a fluid cap 607, and a multi-core fiber 655. The flex tip cap 633 can be configured to couple to a distal end of the flex tip wall 631. The spring 637 can be disposed against an inner surface of the flex tip wall 631. The irrigation balancing plate 651 can be coupled to a distal end of the force body 603. The irrigation balancing plate 651 can further be disposed within an interior portion of the flex tip wall 631. The second fiber support tube center 645 can be coupled to an inner surface of the force body 603 and can also be coupled to a distal end of the support tube 647. The support tube slot 649 can comprise a helical void within the support tube 647 and the support tube sealant 669 can be disposed within the support tube slot 649. The first fiber support tube center 643 can be coupled to an inner surface of the force body 603 and can also be coupled to a proximal end of the support tube 647. A proximal portion of the force body 603 can be coupled to the flex tip wall 631. The force body 603 can comprise a force body slot. The force body slot can comprise a helical void within an outer wall of the force body 603. The force body sealant 661 can be disposed within the force body slot. The fluid cap 607 can be coupled to a proximal end of the force body 603. A distal portion of the multi-core fiber 655 can be disposed within the support tube 647. A portion of the multi-core fiber 655 proximal of the support tube can pass through a center channel of the fluid cap 607.

Figure 15:
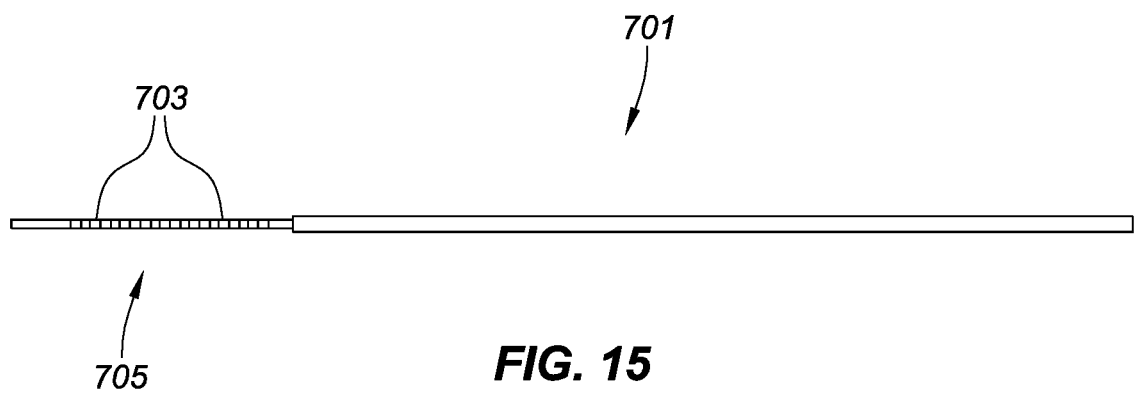
FIG. 15 is a side view of one embodiment of a multi-core fiber.

FIG. 15 illustrates a side view of one embodiment of a multi-core fiber 701. The multi-core fiber 701 can comprise a distal portion 705. As described above, the distal portion 705 can comprise a plurality of Fiber Bragg gratings 703. The Fiber Bragg gratings can be used to determine force and for shape sensing as described throughout the application.

Figure 16:
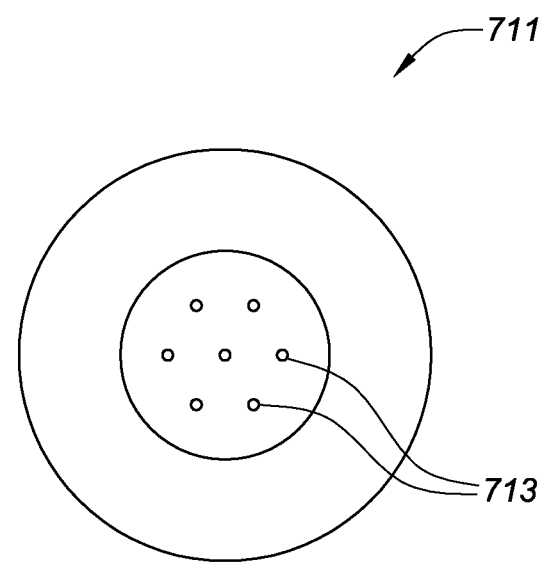
FIG. 16 is a cross-sectional view of one embodiment of a multi-core fiber.

FIG. 16 illustrates a cross-sectional view of one embodiment of a multi-core fiber 711. The multi-core fiber 711 can comprise a plurality of fiber cores 713. In the illustrated embodiment, the multi-core fiber 711 can comprise seven separate fiber cores. In various other embodiments, the multi-core fiber can comprise two cores, three cores, four cores, five cores, six cores, eight cores, nine cores, or more as would be desired by one of ordinary skill in the art for various uses and medical procedures.

Figure 17:
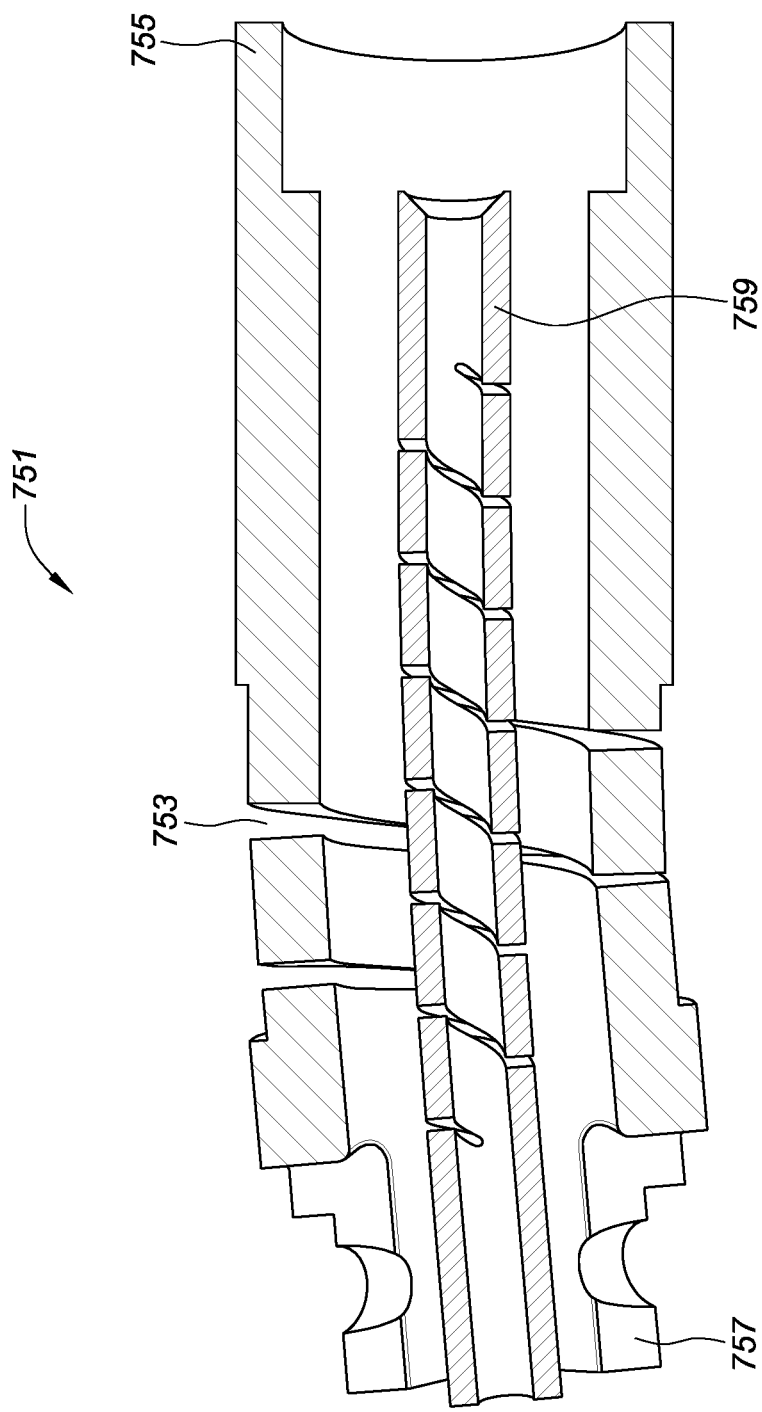
FIG. 17 is a cross-sectional view of an embodiment of a force body and a multi-core fiber.

FIG. 17 depicts an embodiment of a force body 751. The force body 751 can comprise a force body slot 753, a force body distal end 757, a force body proximal end 755, and a support tube 759. The force body 751 is depicted under a force imparted on the force body distal end 757. As seen in the illustrated embodiment, the force body slot 753 allows the force body 751 to bend in reaction to an applied force. While not shown, a force body sealant within the force body slot can conform to the slot when it is compressed or stretched. Further, as the support tube 759 is coupled to the force body 751, the movement of the force body 751 is transferred to the support tube 759.

Figure 18:
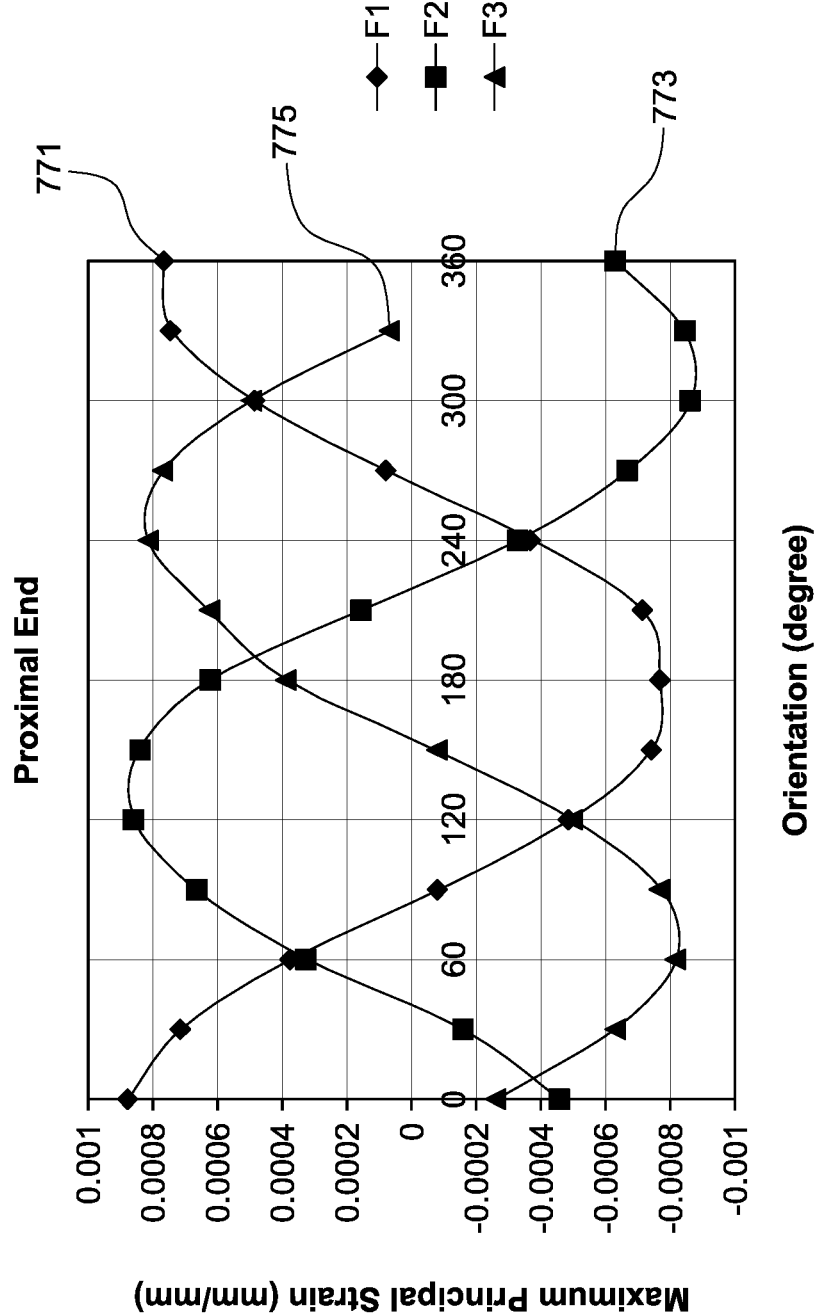
FIG. 18 is a graph of the strain of three fibers within a multi-core fiber.

FIG. 18 depicts a graph of the maximum principal strain experienced by three of the fibers within a multi-core fiber as the multi-core fiber is rolled 360°. The graph depicts the strain to a first fiber core 771, a second fiber core 773, and a third fiber core 775.

Figure 19A:
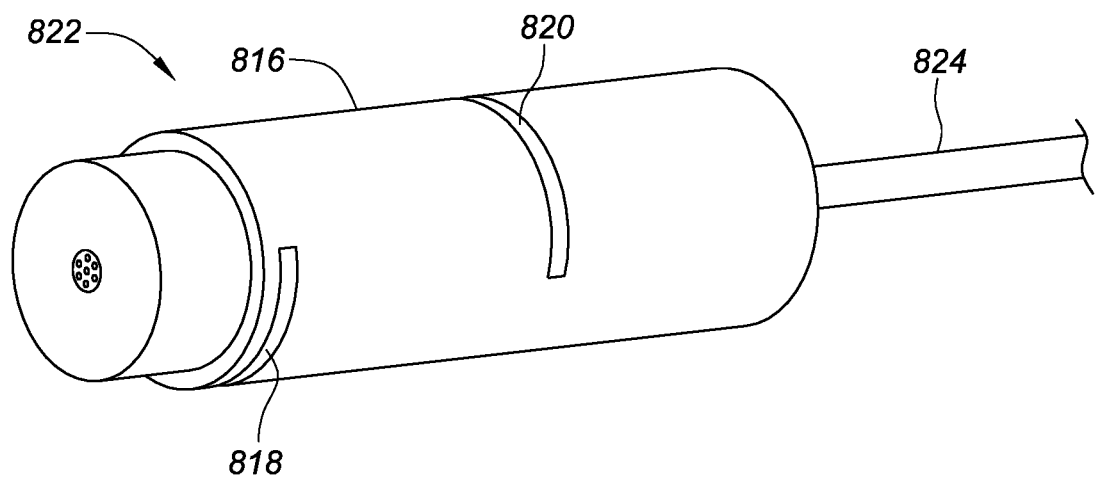
FIG. 19A is an isometric view of one embodiment a flexing structure comprising a multi-core fiber.

FIG. 19A depicts an isometric view of one embodiment of a flexing structure assembly 822. The flexing structure assembly 822 can comprise an exemplary multi-core fiber 824 implemented in a flexing structure 816. In one embodiment, the flexing structure assembly 822 can be positioned proximate a distal portion of a catheter shaft. In the illustrated embodiment, the flexing structure 816 accommodates distal flexing from which at least the force sensors may sense deflection due to force against a structure, such as cardiac tissue. In this embodiment, one or more slots, depicted as slots 818, 812, allow the flexing structure 816 to bend due to a force in response to contact with the tissue. For example, where one or more fiber Bragg grating force sensors are within three respective cores 802, 804, 806 (as seen in FIGS. 3A-3C), and within the flexing structure 816, the force sensors can identify deflection of the flexing structure 816 in response to varying degrees of contact with tissue. Such sensors based on fiber Bragg grating may be implemented as described herein, and/or as described in U.S. Pat. No. 8,182,433 assigned to the assignee of the instant application, which is incorporated herein by reference in its entirety. In other embodiments, the force sensors associated with the force sensing cores 802, 804, 806 (as seen in FIGS. 3A-3C) may utilize a different optical technology.

Figure 19B:
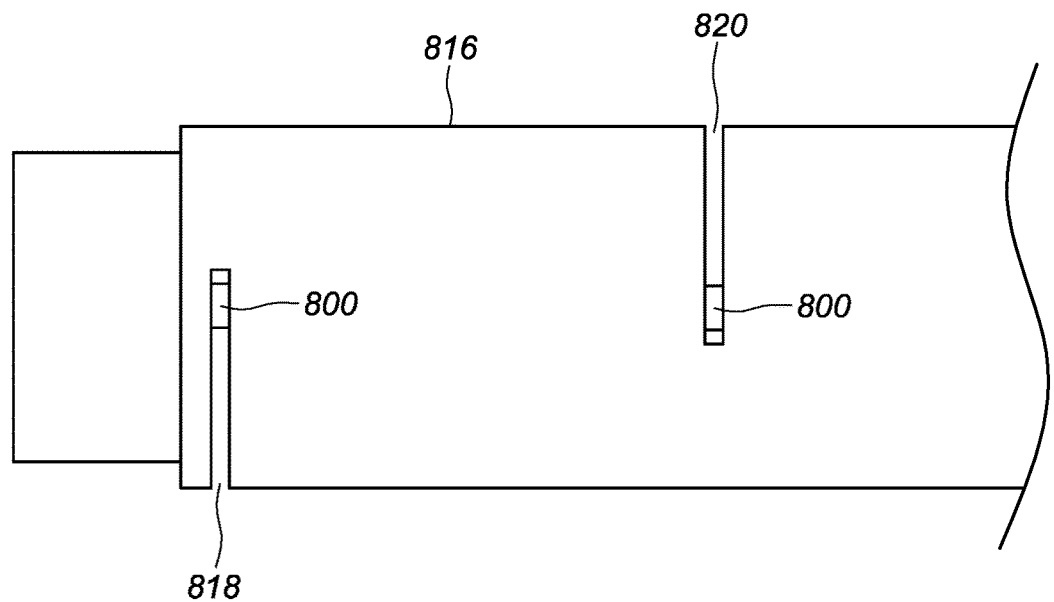
FIG. 19B is a side view of the embodiment of a flexing structure illustrated in FIG. 19A.

FIG. 19B depicts a side view of the flexing structure 816 depicted in FIG. 19A. The flexing structure 816 can comprise a plurality of slots 818, 820 to accommodate bending of the flexing structure 816 in response to contact with a distal end of a catheter.

Figure 19C:
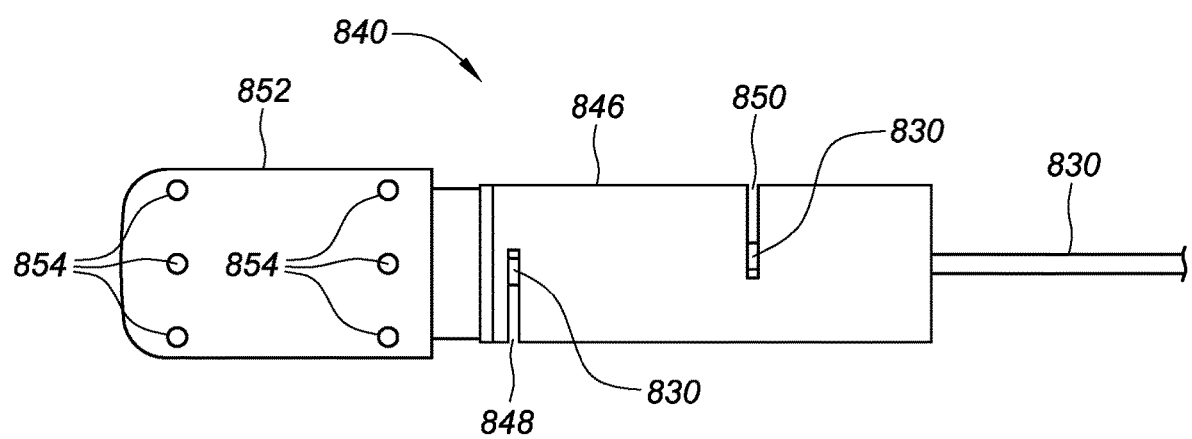
FIG. 19C is a side view of one embodiment of a tip assembly comprising a flexing structure.

FIG. 19C depicts a side view of another embodiment of a catheter tip assembly 840. The catheter tip assembly 840 can comprise a flexing structure 846, a catheter tip 852, a first slot 848, a second slot 850, and a multi-core fiber 830. The flexing structure 846 can be positioned relative to the catheter tip 852, such as an ablation and/or mapping tip. The catheter tip 852 can comprise a plurality of irrigation ports 854 to enable cooling fluid to be discharged from the catheter during a medical procedure. In one embodiment, the flexing structure 846 can be located proximate the catheter tip 852. Further examples of multi-core fibers and flexing structures can be found in U.S. patent application Ser. No. 15/400,655, filed 6 Jan. 2017, titled, "MEDICAL DEVICE WITH MULTI-CORE FIBER FOR OPTICAL SENSING" and assigned to the assignee of the instant application, which is incorporated herein by reference in its entirety.

The above described embodiments can allow for greater axial movement of the catheter and of the tip assembly, will not be affected by moisture, and can have higher manufacturing yields due to not having to work with a super tight tolerance, during fiber placement and fiber manufacturing "cleave angle" as is needed in previous force sensing catheters. Further, the above mentioned embodiments, can reduce the number of fibers in the catheter, reduce the time to assemble the sensor, and still uses a deformable body but it does not need to have a fiber slot. An additional advantage of at least some of the embodiments described herein comprise the multi-core fiber being placed within the irrigation lumen. Irrigant within the irrigation lumen moves through the irrigation lumen and around an outer wall of the multi-core fiber. Irrigant moves from the irrigation lumen into the proximal cavity of the tip assembly before moving to an inner cavity of the tip electrode and exiting the tip electrode through the catheter tip. As a result, the multi-core fiber is surrounded by irrigant within the tip assembly.

An embodiment of a medical device incorporating such principles includes a manipulatable catheter having a shaft that has distal and proximal portions relative to the manipulating mechanism(s). Within the shaft is a multi-core optical fiber, having a plurality of optical cores dedicated for shape sensing sensors, and a plurality of optical cores dedicated for force sensing sensors.

In a more particular embodiment, at least one of the cores of the multi-core optical fiber is dedicated for temperature compensation, which is used to adjust sensed values obtained from the shape sensing sensors and/or the force sensing sensors. In one embodiment, the shape sensing sensors are implemented using one or more fiber Bragg gratings, which reflect light in a perceivable manner when deflected. In another embodiment, the force sensing sensors are implemented using one or more fiber Bragg gratings, which also reflect light in a perceivable manner when deflected. Other embodiments implement fiber Bragg grating technology for both the force sensing and shape sensing sensors, where in yet another embodiment the temperature sensing core also utilizes fiber Bragg grating technology.

One embodiment involves utilizing the multi-core fiber to accommodate only force sensors for detecting distal portion contact with tissue, while in another embodiment the multi-core fiber is utilized to accommodate only shaft shape sensors.

In one embodiment where the multi-core fiber accommodates cores for both shape and force sensing, the shape and force sensing cores are staggered from one another such that every other core is devoted to shape sensors, and the other cores are devoted to force sensors. In one particular embodiment, this staggered pattern is substantially symmetric, and in still another embodiment a core to accommodate one or more temperature sensors (e.g., fiber Bragg grating) is positioned substantially centrally in the fiber relative to the surrounding, symmetric force and shape sensing cores.

Any manner of enabling deflection of the shaft and catheter tip may be utilized. In one embodiment, a flexing structure is provide proximate the force sensors in respective cores of the multi-core fiber to enable the distal portion of the catheter, and thus the included fiber, to deflect. This deflection is perceivable by the fiber Bragg grating or other sensors to provide an indication of an amount of force impacting the distal portion of the catheter.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

Further, although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

What is claimed is:

1. A tip assembly, comprising
   a tip electrode;
   a fiber support tube;
   a multi-core fiber comprising a plurality of cores and disposed within the fiber support tube;
   a first fiber support tube center;
   a second fiber support tube center; and
   a coupler comprising a distal end coupled to a proximal portion of the tip electrode, wherein the first fiber support tube center, the second fiber support tube center, and the fiber support tube are disposed within an interior portion of the coupler, wherein a proximal portion of the fiber support tube is coupled to and disposed within a through hole of the first fiber support tube center and a distal portion of the fiber support tube is coupled to the second fiber support tube center, wherein the coupler comprises one or more slots disposed in between the first fiber support tube center and the second fiber support tube center and axially spaced from the first fiber support tube center and the second fiber support tube center;
   wherein the first fiber support tube center and the second fiber support tube center are configured to center the multi-core fiber within the coupler.

2. The tip assembly according to claim 1, wherein the tip electrode comprises a flex electrode.

3. The tip assembly according to claim 1, wherein the coupler further comprises an irrigation balancing plate coupled to a distal end of the coupler.

4. The tip assembly according to claim 3, wherein the irrigation balancing plate comprises at least one plate irrigation through holes.

5. The tip assembly according to claim 1, wherein the multi-core fiber comprises at least four core fibers.

6. The tip assembly according to claim 1, further comprising a fluid cap coupled to a proximal end of the coupler.

7. The tip assembly according to claim 6, wherein the fluid cap comprises a central channel and wherein the multi-core fiber passes through the central channel.

8. The tip assembly according to claim 6, further comprising an irrigation lumen coupled to the fluid cap.

9. The tip assembly according to claim 8, wherein the multi-core fiber is disposed within the irrigation lumen.

10. A tip assembly, comprising:
    a fiber support tube;
    a first fiber support tube center;
    a second fiber support tube center;
    a multi-core fiber comprising a plurality of cores and disposed within an interior cavity of the fiber support tube;
    a coupler comprising the first fiber support tube center; and
    a flex tip comprising the second fiber support tube center, the flex tip coupled to a distal portion of the coupler, wherein the flex tip comprises a flex tip wall disposed between the first fiber support tube center and the second fiber support tube center,
    wherein the fiber support tube is coupled to the first fiber support tube center and the second fiber support tube center, wherein the fiber support tube is disposed within a through hole of the first fiber support tube center, and wherein the first fiber support tube center and at least a portion of the fiber support tube are disposed within an interior portion of the coupler and configured to center the multi-core fiber along a longitudinal axis of the coupler.

11. The tip assembly according to claim 10, wherein the first fiber support tube center comprises a plurality of centering protrusions.

12. The tip assembly according to claim 11, wherein the coupler further comprises an interior surface, wherein the each of the plurality of centering protrusions comprises a protrusion outer surface, and wherein the protrusion outer surface is configured to interact with the interior surface of the coupler.

13. The tip assembly according to claim 10, wherein the fiber support tube further comprises a support tube slot.

14. The tip assembly according to claim 13, wherein the support tube slot comprises a helical slot in the support tube.

15. The tip assembly according to claim 10, wherein the coupler comprises a helical slot in the coupler and wherein the coupler further comprises a sealant within the coupler slot.

16. The tip assembly according to claim 10, wherein a distal end of the support tube is coupled to the second fiber support tube center and wherein a proximal end of the support tube is coupled to the first fiber support tube center.

17. A tip assembly, comprising:
- a fiber support tube;
- a multi-core fiber comprising a plurality of cores, disposed within the fiber support tube;
- a first fiber support tube center;
- a second fiber support tube center;
- a coupler, wherein the first fiber support tube center, and the second fiber support tube center, and the fiber support tube are disposed within an interior portion of the coupler, wherein a proximal end of the fiber support tube is coupled to and disposed within a through hole of the first fiber support tube center and a distal end of the support tube is coupled to a second fiber support tube center, and wherein the coupler comprises one or more slots disposed in between the first fiber support tube center and the second fiber support tube center and axially spaced from the first fiber support tube center and the second fiber support tube center;
- a fluid cap comprising a central channel and at least one electrical channel, wherein the fluid cap is coupled to a proximal end of the coupler;
- an irrigation lumen coupled to the fluid cap; and
- a tip electrode coupled to a distal portion of the coupler,
- wherein the multi-core fiber is disposed within an interior portion of the irrigation lumen, and wherein the fiber support tube is coupled to the first fiber support tube center, and wherein the first fiber support tube center and the second fiber support tube center are configured to center the multi-core fiber along a longitudinal axis of the irrigation lumen.

18. The tip assembly according to claim 17, wherein a distal end of the fiber support tube is coupled to a second fiber support tube center and wherein a proximal end of the fiber support tube is coupled to the first fiber support tube center.

19. The tip assembly according to claim 17, wherein the tip electrode.

20. The tip assembly according to claim 17, wherein multi-core fiber is disposed within an interior portion of the tip electrode.

* * * * *